United States Patent
Behrooz et al.

(10) Patent No.: US 10,548,553 B2
(45) Date of Patent: *Feb. 4, 2020

(54) SYSTEMS AND METHODS FOR CHARACTERIZING A CENTRAL AXIS OF A BONE FROM A 3D ANATOMICAL IMAGE

(71) Applicant: PerkinElmer Health Sciences, Inc., Waltham, MA (US)

(72) Inventors: Ali Behrooz, Waltham, MA (US); Joshua Kempner, Medway, MA (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/155,943

(22) Filed: Oct. 10, 2018

(65) Prior Publication Data

US 2019/0046144 A1 Feb. 14, 2019

Related U.S. Application Data

(62) Division of application No. 15/081,788, filed on Mar. 25, 2016, now Pat. No. 10,136,869.

(51) Int. Cl.
*A61B 6/00* (2006.01)
*A61B 6/03* (2006.01)
*G06T 7/00* (2017.01)

(52) U.S. Cl.
CPC ............. *A61B 6/505* (2013.01); *A61B 6/032* (2013.01); *G06T 7/0012* (2013.01);
(Continued)

(58) Field of Classification Search
CPC ....... A61B 6/505; A61B 6/032; A61B 6/5217; G06T 7/0012; G06T 2207/10081;
(Continued)

(56) References Cited

U.S. PATENT DOCUMENTS 7,539,332 B1 5/2009 Al-Dayeh et al.
8,306,305 B2 11/2012 Porat et al.
(Continued)

FOREIGN PATENT DOCUMENTS

EP 2194505 A1 6/2010
JP H09-294740 A 11/1997
(Continued)

OTHER PUBLICATIONS

Ballard, Dana H., "Model-Directed Detection of Ribs in Chest Radiographs" Computer Science Department, University of Rochester, (1978) 24 pages.
(Continued)

*Primary Examiner* — Yon J Couso
(74) *Attorney, Agent, or Firm* — Banner & Witcoff, Ltd.

(57) ABSTRACT

Presented herein are efficient and reliable systems and methods for calculating and extracting three-dimensional central axes of bones of animal subjects—for example, animal subjects scanned by in vivo or ex vivo microCT platforms—to capture both the general and localized tangential directions of the bone, along with its shape, form, curvature, and orientation. With bone detection and segmentation algorithms, the skeletal bones of animal subjects scanned by CT or microCT scanners can be detected, segmented, and visualized. Three dimensional central axes determined using these methods provide important information about the skeletal bones.

20 Claims, 15 Drawing Sheets
(9 of 15 Drawing Sheet(s) Filed in Color)

(52) U.S. Cl.
CPC ............... *G06T 2207/10081* (2013.01); *G06T 2207/30008* (2013.01); *G06T 2207/30024* (2013.01)

(58) Field of Classification Search
CPC ............. G06T 2207/30008; G06T 7/62; G06T 2207/20036; G06T 2207/20044; G06T 2207/30172; G06T 2207/30024
See application file for complete search history.

(56) References Cited

U.S. PATENT DOCUMENTS

| | | | |
|---|---|---|---|
| 9,192,348 | B2 | 11/2015 | Ollilainen et al. |
| 2005/0163358 | A1 | 7/2005 | Moeller |
| 2007/0031019 | A1 | 2/2007 | Lesage et al. |
| 2008/0107318 | A1 | 5/2008 | Kiraly |
| 2010/0128954 | A1 | 5/2010 | Ostrovsky-Berman et al. |
| 2012/0143037 | A1 | 6/2012 | Najarian et al. |
| 2012/0224758 | A1 | 9/2012 | Treece et al. |
| 2013/0163836 | A1 | 6/2013 | Pau et al. |
| 2013/0272594 | A1* | 10/2013 | Zelzer .................. G06T 3/0043 382/131 |
| 2016/0038124 | A1 | 2/2016 | Tsujita |
| 2016/0242852 | A1 | 8/2016 | Yosibash et al. |
| 2017/0032518 | A1 | 2/2017 | Behrooz et al. |

FOREIGN PATENT DOCUMENTS

| | | |
|---|---|---|
| JP | 2008220406 A | 9/2008 |
| RU | 2342077 C1 | 12/2008 |
| WO | 2009/101560 A2 | 8/2009 |
| WO | 2014/050601 A1 | 4/2014 |
| WO | 2017/019059 A1 | 2/2017 |
| WO | 2017164893 A1 | 9/2017 |

OTHER PUBLICATIONS

De Bruijne, M. et al. "Multi-Object Segmentation Using Shape Particles" IPMI, LNCS 3565:762-773 (2005).
Fiebich, M. et al.. "Automatic Bone Segmentation Technique for CT Angiographic Studies", Journal of Computer Assisted Tomography, 23(1): 155-161 (1999).
Frangi, A.F. et al. , "Multiscale vessel enhancement filtering, Medical Image Computing and Computer-Assisted Intervention" Lecture Notes in Computer Science, 1496:130-137 (1998).
Khmelinskii, A. et al. "Atlas-Based Organ & Bone Approximation for Ex-Vivo 1/4 MRI Mouse Data: A Pilot Study" IEEE ISBI, 1197-1200 (2010).
Klinder, T. et al. "Automated Model-Based Rib Cage Segmentation and Labeling in CT Images" MICCA, Part II, LNCS 4792:195-202 (2007).
Krcah, M. et al. "Fully Automated and Fast Segmentation of the Femur Bone From 3D Images with No Shape Prior" IEEE, pp. 2087-2090, ISBI 2011.
Laib, A. et al. "3D Micro-Computed Tomography of Trabecular and Cortical Bone Architecture with Application to a Rat Model of Immobilisation Osteoporois" Medical and Biological Engineering and Computing, 38(3):326-332 (2000).
Lee, J. et al. "Segmentation of Individual Ribs from Low-Dose Chest CT" Medical Imaging, 7264:J1-J8 (2010).
Lee, T.C. et al. "Building Skeleton Models Via 3-D Medical Surfaces/Axis Thinning Algorithms" CVGIP: Graphical Models and Image Processing, Academic Press, 56(6):462-478 (1994).
Lemke, H. et al. CAR '97, Computer Assisted Radiology and Surgery, Elsevier, 209-214 (1997).
Maier, F. et al. "Automatic Liver Segmentation Using the Random Walker Algorithm" Univeritat Karlsruhe (TH), Siemens Medical Solutions, Forchheim, Friedrich-Alexander University, Erlangen-Nuremberg, RWTH Aachen University, 6 pages, 2008.
Meyer, F. et al., "Morphological Segmentation" Journal of Visual Communication and Image Representation, 1(1):21-46 (1990).
Jan. 11, 2017—(WO) International Search Report—App PCT/US2016/024372.
Staal, J. et al., "Automatic Rib Segmentation and Labeling in Computed Tomography Scans Using a General Framework for Detection, Recognition and Segmentation of Objects in Volumetric Data" Medical Image Analysis 11:35-46 (2007).
Staal, J. et al. "Automatic Rib Segmentation in CT Data" CVAMIA-MMBIA, LNCS 3117:193-204 (2004).
Sun, S. et al. "Automated 3-D Segmentation of Lungs With Lung Cancer in CT Data Using a Novel Robust Active Shape Model Approach" IEEE Transactions on Medical Imaging, 31(2):449-460 (2012).
Wang, H. et al. "Estimation of Mouse Organ Locations Through Registration of a Statistical Mouse Atlas With Micro-CT Images" IEEE Transactions on Medical Imaging, 31(1):88-102 (2012).
Wildeman, M. H. et al., "2D/3D Registration of Micro-CT Data to Multi-View Photographs Based on a 3D Distance Map" Biomedical Imaging, IEEE International Symposium ON, 987-990 (2009).
Wlodarczyk, J. et al., "Segmentation of bones in magnetic resonance images of the wrist" International Journal of Computer Assisted Radiology and Surgery, 10(4):419-431 (2014).
Wu, D. et al., "A Learning Based Deformable Template Matching Method for Automatic Rib Centerline Extraction and Labeling in CT Images" IEEE, 980-987 (2012).
Yin, Y. et al. "Hierarchical Decision Framework with Priori Shape Models for Knee Joint Cartilage Segmentation" MICCAI Grand Challenge, Depts. Of Electrical & Computer Engineering and Orthopaedics & Rehabilitation, University of Iowa, pp. 241-250 (2010).
AnalyzeDirect, "Analyze 12.0 Bone Microarchitecture Analysis Manual" AnalyzeDirect, Inc. and BIR, Mayo Clinic, 56 Pages, 1999-2014.
Computer Vision Demonstration Website, Electronics and Computer Science University of Southampton, Standard and Hysteresis Thresholding, 2 pages (2005) [retrieved May 3, 2017 <http://users.ecs.saoton.ac.uk/msn/book/new_demo/thresholding/>.
Eddins, Steve "The Watershed Transform: Strategies for Image Segmentation" MathWorks, 8 pages (2002) [retrieved May 3, 2017 <https:www.mathworks.com/company/newsletters/articles/the-watershed-transform-strategies-for-image-segmentation.html>.
Mar. 15, 2017—(WO) International Search Report and Written Opinion—PCT/US2014/024372.
Mavrogenis, A.F. et al. "Heterotopic Ossification Revisited, Orthoedics" 34:(3)177—(2011).
Otsu, Nobuyuki "A Threshold Selection Method from Gray-Level Histograms" IEEE Transactions on Systems, Man and Cybernetics, SMC-9(1):62-66 (1979).
Smolka, Jakub "Watershed based region growing algorithm" Annales UMCS Informatica AI, 3:169-178 (2005).
Waarsing, J. H. et al. "An Improved Segmentation Method for in Vivo CT Imaging" Journal of Bone and Mineral Research, 19:1640-1650 (2004).
Wikipedia "Canny Edge Detector" 9 pages (2017) [retrieved May 3, 2017 <https://en.wikipedia.org/wiki/Canny_edge_detector>].
Li, Q et al., "Selective enhancement filters for nodules, vessels, and airway walls in two and three-dimensional CT scans" Med. Phys. 30(8):2040-2051 (2003).
Sato, Y. et al. "3D Multi-Scale Line Filter for Segmentation and Visualization of Curvilinear Structures in Medical Images" Medical Image Analysis 2(2)L143-168 (1998).
May 16, 2019—(RU) Office Action—App 2018136627.
May 31, 2019—(CA) Office Action—App 3,014,608.
Aug. 15, 2019—(RU) Office Action—App 2018136627.
Aug. 21, 2019—(JP) Office Action—App 2018-549919.

* cited by examiner

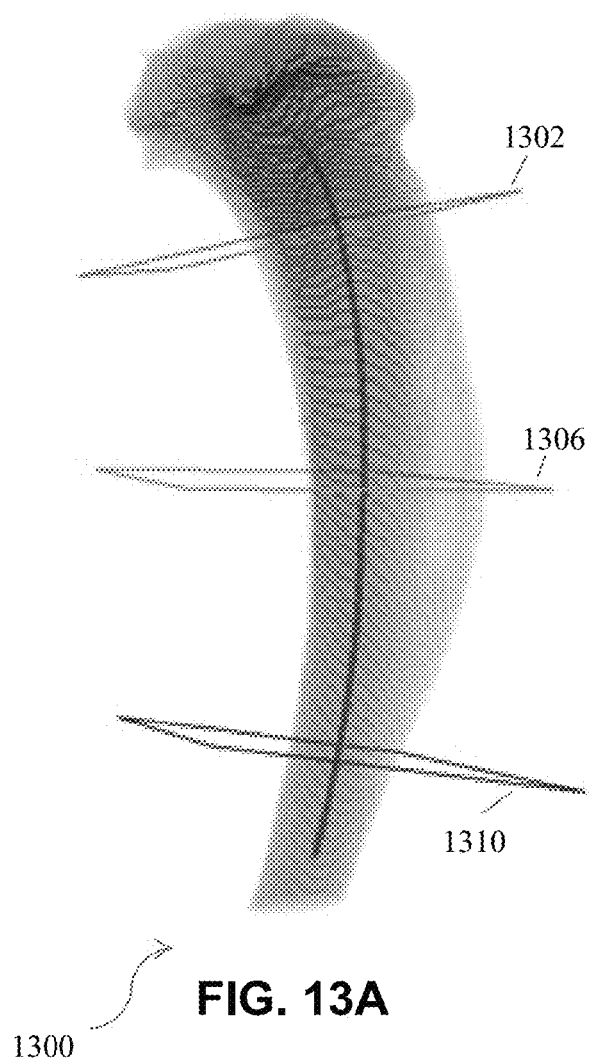
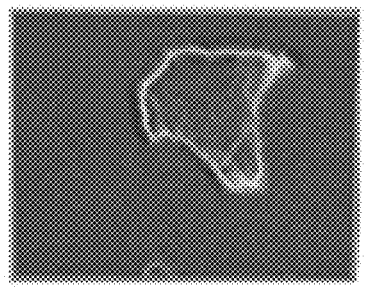
FIG. 13B
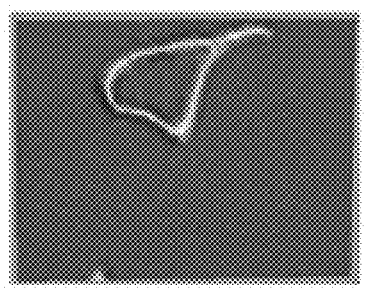
FIG. 13C
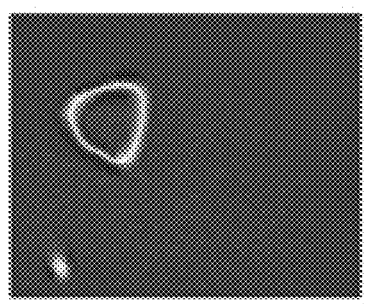
FIG. 13D
FIG. 13A

SYSTEMS AND METHODS FOR CHARACTERIZING A CENTRAL AXIS OF A BONE FROM A 3D ANATOMICAL IMAGE

RELATED APPLICATIONS

This application is a divisional of, and claims priority to, U.S. application Ser. No. 15/081,788 filed Mar. 25, 2016, the entire disclosure of which is hereby incorporated herein by reference.

TECHNICAL FIELD

This invention relates generally to methods and systems of image analysis. More particularly, in certain embodiments, the invention relates to detection and localization of a bone central axis from an image of a subject (e.g., mammal), e.g., captured with a computed tomography (CT) scanner.

BACKGROUND

There is a wide array of technologies directed to in vivo and ex vivo imaging of mammals—for example, bioluminescence, fluorescence, X-ray computed tomography, and multimodal imaging technologies. In vivo imaging of small mammals and ex vivo imaging of samples from small mammals is performed by a large community of investigators in various fields, e.g., oncology, infectious disease, and drug discovery.

Micro computed tomography (hereafter, "microCT") imaging, is an x-ray-based technology that can image tissues, organs, and non-organic structures with an extremely high resolution. MicroCT has evolved quickly, requiring low dose scanning and fast imaging protocols to facilitate multimodal applications and enable longitudinal experimental models. Similarly, nano-computed tomography (nanoCT) systems designed for high-resolution imaging of ex vivo samples are also now used. Multi-modal imaging involves the fusion of images obtained in different ways, for example, by combining fluorescence molecular tomography (FMT), PET, MRI, CT, and/or SPECT imaging data.

Conventional image analysis applications and/or imaging systems typically allow for visualization, analysis, processing, segmentation, registration and measurement of biomedical images. These applications and systems also provide volume rendering tools (e.g., volumetric compositing, depth shading, gradient shading, maximum intensity projection, summed voxel projection, signal projection); manipulation functions (e.g., to define areas of structures of interest, delete unwanted objects, edit images and object maps); and measurement functions (e.g., calculation of number of surface voxels, number of exposed faces, planar area of a region, estimated surface area of a region).

Acquisition of animal images can be time consuming, and rapid analysis of the acquired images is key to the efficiency of the process. Three dimensional (3D) imaging software, including microCT image analysis, enables extraction of structural, biological, and anatomical attributes from images, such as thickness, porosity, anisotropy, and other measures, of organs of interest, such as bones. Due to the anatomical contrast and high spatial resolution provided by microCT systems, they are widely used for studying skeletal bone formation, structure, and diseases. Automation of such analyses improves throughput, accuracy, and efficacy. In classical bone analysis approaches, researchers were required to visually and manually quantify the structural attributes of bones using printed images produced by the microCT platform. While some image analysis systems have been developed for computer-aided bone analysis, the digital workflows offered by bone analysis software still require considerable manual input and interaction from users and researchers. For example, such manual feedback is currently required to obtain stereological measures of cortical and trabecular bone compartments, e.g., manual selection of discrete 2-D slices of a 3-D bone image from which averaged thicknesses or other properties are determined.

Some conventional image analysis systems focus on locating the principal axes of the bones to extract the direction of 2-D slices of the bone. But principal axes do not carry detailed shape and directional information. Principal axes represent the major and minor directional axes of a bone, as shown in FIG. 1, and are defined as the eigenvectors of the moment of inertia tensor of the bone volume. As shown in FIG. 1, principal axes do not capture detailed information regarding the shape, form, localized tangential directions, and curvature of the bone—all of which impact the precision of automated stereological studies of osteological structure and disease assessment. The principal axes primarily indicate the general direction of a bone as a solid object without fully capturing its shape and curvature. Moreover, the principal axes are not useful in characterizing partially circular bones, e.g., the pelvic girdle. As such, they are not useful for automating 2-D slice-by-slice measurements and analysis.

There is a need for automated, precise, and improved methods for stereological analysis and slice-by-slice characterization of bones in images, such as microCT images.

SUMMARY OF THE INVENTION

Automated detection of central axes of skeletal bones significantly improves the speed, efficiency, and automation of slice-by-slice measurements and analyses of bones. Central axes of long bones (e.g., bones of the extremities that have a length greater than the width, e.g., femur) can effectively encapsulate the spatial features, direction, orientation, and shape of long bones. Calculation of central axes is essential for performing automated and accurate 2-D slice-by-slice planar studies such as stereological studies on bones, for example, the femur and the tibia. The 2-D planes perpendicular to the central axes constitute the slices that are used in 2-D bone analysis or stereology measurements. Automated detection of bone central axis and the 2-D stereology slices allows for fully automated computer-based stereological measurements of bones.

Presented herein are efficient and reliable systems and methods for calculating and extracting three-dimensional central axes of skeletal bones of animal subjects—for example, animal subjects scanned by in vivo microCT platforms and ex vivo samples of animal subjects scanned by microCT or nanoCT platforms—to capture both the general and localized tangential directions of the bone, along with its shape, form, curvature, and orientation. With bone detection and segmentation algorithms, the bones of animal subjects scanned by CT, nanoCT, or microCT scanners can be detected, segmented, and visualized automatically. Three dimensional central axes determined using these methods provide important information about the bones.

The detection and localization of central axes improves the speed and accuracy of stereology studies performed visually and manually and circumvents the limitations of principal axes and provides, inter alia, directional, shape, and curvature information regarding the bone. The detection and localization of central axes reveals a variety of features relating to the shape, direction, and curvature of the bone that are not available through the existing method of using the principal axes. This is particularly useful for analysis of curved or non-straight long bones, and for 2-D slice-by-slice analysis, e.g., 2-D planar slice-by-slice stereology studies of the tibia or pelvic girdle. The central axis of a bone represents the medial path that describes the main center-line, shape, and orientation of a bone.

An automated procedure for identifying a central bone axis is not a simple problem, since the procedure would need to accurately identify the central bone axis for a wide range of sizes and shapes of the bones being imaged (e.g., it would need to account for different kinds of bones as well as variability between the same bone across multiple subjects) without user interaction or training, and it would need to be a computationally efficient procedure.

Presented herein, in certain embodiments, are systems and methods for automated computation of a bone central axis from a 3D anatomical image. An area of the subject (e.g., mammal) including a bone of interest is scanned (e.g., with a microCT system), and a 3D anatomical image of the area of the subject is obtained. In some embodiments, in a first step, a binary mask of the bone of interest is filled using morphological processing. In some embodiments, the binary mask of the bone is filled by morphological processing to more accurately reflect the internal composition of the bone (e.g., to accurately model the distinct trabecular and cortical components of the bone). In some embodiments, in a second step, skeletonization (e.g., morphological skeletonization) is performed on the filled bone by iterative 3-D thinning. In some embodiments, in a third step, the skeleton is pruned (e.g., thinned) and reduced to a single (e.g., a main and/or central) branch. In some embodiments, the skeleton is pruned down to the single branch and smoothed, yielding a single-branched curve that follows the medial path of the bone, effectively identifying and isolating the central axis of the bone.

Also described herein are systems and methods to efficiently fill the morphological holes on the six exterior faces of a three-dimensional (hereafter, "3-D") binary image. Some embodiments described herein relate to systems and methods for filling 2-D morphological holes which extend across three faces. In some embodiments, these morphological holes on the boundary are due to hollow internal compartments of partially out-of-view bones.

Some example embodiments described herein relate to calculating and extracting central axes of skeletal bones (e.g., long bones) to capture both the general and localized tangential directions of the bones. The calculation of central axes also identifies, among other things, the shape, form, and curvature of the bones. That is, the central axis represents a medial path that describes, among other things, the main center-line, shape, and orientation of a long bone.

In one aspect, the invention is directed to a method for automatically identifying a three-dimensional (3-D) central axis of a bone of interest in a 3-D image, the method comprising: receiving, by a processor of a computing device, the 3-D image of one or more bones, comprising the bone of interest (i.e., at least a portion of the bone of interest), of a mammal; isolating, by the processor, the bone of interest from the one or more bones in the 3-D image (e.g., yielding an isolated image of an exterior surface of a cortical tissue of the bone of interest); generating, by the processor (e.g., after the isolating of the bone of interest), a binary bone mask of the bone of interest; generating, by the processor, a filled bone mask for the bone of interest using the binary bone mask; generating, by the processor, a skeleton of the bone of interest (e.g., by performing iterative 3-D thinning of the filled bone mask); and generating, by the processor, a pruned skeleton to reduce the skeleton to a branch (e.g., a single branch, central branch, and/or main branch) corresponding to the 3-D central axis of the bone of interest.

In certain embodiments, the bone of interest is a long bone of the mammal (e.g., a femur, tibia, fibula, humerus, radius, ulna, metacarpal, metatarsal, phalange, and clavicle). In certain embodiments, the bone of interest is a non-long bone (e.g., a short bone, flat bone, sesamoid bone, or irregular bone) of the mammal (e.g., pelvic girdle).

In certain embodiments, the 3-D image is obtained by a computed tomography scanner (e.g., a micro computed or nano computed tomography scanner). In certain embodiments, the 3-D image is captured in vivo. In certain embodiments, the 3-D image is captured ex vivo. In certain embodiments, the 3-D image is a computed tomography image of an exterior surface of cortical tissue of the one or more bones.

In certain embodiments, generating the filled bone mask for the bone of interest comprises performing, by the processor, morphological processing of the portion of the 3-D image corresponding to the bone of interest, said processing comprising: performing 3-D binary dilation of the binary bone mask of the bone of interest (e.g., with a spherical structuring element) to form a dilated bone mask; and identifying and filling borders and/or morphological holes (e.g., gaps and/or discontinuities) of the dilated bone mask, then processing the result (e.g., performing 3-D binary erosion on the result of the border and hole filling operations) to generate the filled bone mask for the bone of interest.

In certain embodiments, the method comprises filling borders of the bone of interest by: representing image data from the binary bone mask of the bone of interest digitally as one or more data-cubes; identifying a vertex of a data-cube, the vertex having all edges connected to the vertex associated with true (e.g., binary true) voxels; forming a 2-D image from the three faces connected to the identified vertex (e.g., by adding an all-zero face as one of the quadrants and diagonally connecting binary true voxels on the boundaries of the all-zero face quadrant); filling morphological holes in the thusly formed 2-D image to produce a filled surface; and mapping the filled surface back to the three corresponding faces of the data-cube.

In certain embodiments, generating the 3-D skeleton of the bone of interest comprises performing, by the processor, morphological processing of the filled bone mask, the processing comprising performing iterative 3-D thinning of the filled bone mask.

In certain embodiments, generating the pruned 3-D skeleton comprises performing, by the processor, morphological processing of the skeleton for the bone of interest, said processing comprising: identifying a single-branched centerline tree or a single-cycle main loop of the skeleton as a main path; pruning the skeleton by removing minor branches not included in the main path; and smoothing the pruned skeleton (e.g., by point averaging), thereby generating the pruned 3-D skeleton.

In certain embodiments, the method comprises characterizing the bone of interest according to the 3-D central axis corresponding to the bone of interest (e.g., identifying an abnormality of the bone and/or identifying the bone as a specific bone of the mammal).

In certain embodiments, the method comprises rendering an image using at least the 3-D central axis of the bone of interest.

In certain embodiments, the method comprises performing, by the processor, a stereological measurement of the bone of interest using the identified 3-D central axis of the bone of interest, said performing of the stereological measurement comprising: producing a plurality of graphical 2-D cross-sections (e.g., 2-D image slices) of the bone of interest in planes perpendicular to the identified 3-D central axis at various locations along a length of the bone of interest; for each of the graphical 2-D cross-sections, determine a measurement of the bone as depicted in the graphical 2-D cross section (e.g., identifying a cortical thickness for each of the 2-D image slices); and obtaining the stereological measurement of the bone of interest using the measurements determined from the plurality of graphical 2-D cross-sections (e.g., obtaining an average cortical thickness for the bone of interest as an average of the measurements determined from the 2-D image slices).

In certain embodiments, the method comprises determining, by the processor, one or more of (i) to (iii)—(i) the presence of a disease state, (ii) a disease state risk, and/or (iii) an extent of disease progression (e.g., staging of a disease)—using the identified 3-D central axis of the bone of interest (e.g., based on one or more stereological measurements of the bone of interest determined using the identified 3-D central axis of the bone of interest).

In another aspect, the invention is directed to a method of automatically filling borders in an image of an object (e.g., a bone) of interest, the method comprising: digitally representing image data from a binary mask of an object (e.g., a bone of interest) as one or more data-cubes; identifying, by a processor of a computing device, a vertex of a data-cube of the one or more data-cubes, the vertex having all edges connected to the vertex associated with true (e.g., binary true) voxels; forming, by the processor, a 2-D image from the three faces connected to the identified vertex (e.g., by adding an all-zero face as one of the quadrants and diagonally connecting binary true voxels on the boundaries of the all-zero face quadrant); filling, by the processor, morphological holes in the thusly formed 2-D image to produce a filled surface; and mapping, by the processor, the filled surface back to the three corresponding faces of the data-cube.

In another aspect, the invention is directed to a system for automatically identifying a three-dimensional (3-D) central axis of a bone of interest in a 3-D image, the system comprising: a processor; and a memory having instructions stored thereon, wherein the instructions, when executed by the processor, cause the processor to: receive the 3-D image of one or more bones, comprising the bone of interest (i.e., at least a portion of the bone of interest), of a mammal; isolate the bone of interest from the one or more bones in the 3-D image (e.g., yielding an isolated image of an exterior surface of a cortical tissue of the bone of interest); generate (e.g., after the isolating of the bone of interest), a binary bone mask of the bone of interest; generate a filled bone mask for the bone of interest using the binary bone mask; generate a skeleton of the bone of interest (e.g., by performing iterative 3-D thinning of the filled bone mask); and generate a pruned skeleton to reduce the skeleton to a branch (e.g., a single branch, central branch, and/or main branch) corresponding to the 3-D central axis of the bone of interest.

In certain embodiments, the bone of interest is a long bone of the mammal (e.g., a femur, tibia, fibula, humerus, radius, ulna, metacarpal, metatarsal, phalange, and clavicle). In certain embodiments, the bone of interest is a non-long bone (e.g., a short bone, flat bone, sesamoid bone, or irregular bone) of the mammal (e.g., pelvic girdle). In certain embodiments, the 3-D image is obtained by a computed tomography scanner (e.g., a micro computed or nano computed tomography scanner).

In certain embodiments, the 3-D image is captured in vivo. In certain embodiments, the 3-D image is captured ex vivo. In certain embodiments, the 3-D image is a computed tomography image of an exterior surface of cortical tissue of the one or more bones.

In certain embodiments, the instructions cause the processor to generate the filled bone mask for the bone of interest by performing morphological processing of the portion of the 3-D image corresponding to the bone of interest, said processing comprising: performing 3-D binary dilation of the binary bone mask of the bone of interest (e.g., with a spherical structuring element) to form a dilated bone mask; and identifying and filling borders and/or morphological holes (e.g., gaps and/or discontinuities) of the dilated bone mask, then processing the result (e.g., performing 3-D binary erosion on the result of the border and hole filling operations) to generate the filled bone mask for the bone of interest.

In certain embodiments, the instructions cause the processor to fill borders of the bone of interest by: representing image data from the binary bone mask of the bone of interest digitally as one or more data-cubes; identifying a vertex of a data-cube, the vertex having all edges connected to the vertex associated with true (e.g., binary true) voxels; forming a 2-D image from the three faces connected to the identified vertex (e.g., by adding an all-zero face as one of the quadrants and diagonally connecting binary true voxels on the boundaries of the all-zero face quadrant); filling morphological holes in the thusly formed 2-D image to produce a filled surface; and mapping the filled surface back to the three corresponding faces of the data-cube.

In certain embodiments, the instructions cause the processor to generate the 3-D skeleton of the bone of interest by performing morphological processing of the filled bone mask, the processing comprising performing iterative 3-D thinning of the filled bone mask.

In certain embodiments, the instructions cause the processor to generate the pruned 3-D skeleton by performing morphological processing of the skeleton for the bone of interest, said processing comprising: identifying a single-branched centerline tree or a single-cycle main loop of the skeleton as a main path; pruning the skeleton by removing minor branches not included in the main path; and smoothing the pruned skeleton (e.g., by point averaging), thereby generating the pruned 3-D skeleton.

In certain embodiments, the instructions cause the processor to characterize the bone of interest according to a central axis corresponding to the bone of interest (e.g., identifying an abnormality of the bone and/or identifying the bone as a specific bone of the mammal). In certain embodiments, the instructions cause the processor to render an image using at least the 3-D central axis of the bone of interest. In certain embodiments, the instructions cause the processor to perform a stereological measurement of the bone of interest using the identified 3-D central axis of the bone of interest, said performing of the stereological measurement comprising: producing a plurality of graphical 2-D cross-sections (e.g., 2-D image slices) of the bone of interest in planes perpendicular to the identified 3-D central axis at various locations along a length of the bone of interest; for each of the graphical 2-D cross-sections, determining a measurement of the bone as depicted in the graphical 2-D cross section (e.g., identifying a cortical thickness for each of the 2-D image slices); and obtaining the stereological measurement of the bone of interest using the measurements determined from the plurality of graphical 2-D cross-sections (e.g., obtaining an average cortical thickness for the bone of interest as an average of the measurements determined from the 2-D image slices). In certain embodiments, the instructions cause the processor to determine one or more of (i) to (iii)—(i) the presence of a disease state, (ii) a disease state risk, and/or (iii) an extent of disease progression (e.g., staging of a disease)—using the identified 3-D central axis of the bone of interest (e.g., based on one or more stereological measurements of the bone of interest determined using the identified 3-D central axis of the bone of interest).

In another aspect, the invention is directed to a system for automatically filling borders in an image of an object (e.g., a bone) of interest, the system comprising: a processor; and a memory having instructions stored thereon, wherein the instructions, when executed by the processor, cause the processor to: digitally represent image data from a binary mask of an object (e.g., a bone of interest) as one or more data-cubes; identify a vertex of a data-cube of the one or more data-cubes, the vertex having all edges connected to the vertex associated with true (e.g., binary true) voxels; form a 2-D image from the three faces connected to the identified vertex (e.g., by adding an all-zero face as one of the quadrants and diagonally connecting binary true voxels on the boundaries of the all-zero face quadrant); fill morphological holes in the thusly formed 2-D image to produce a filled surface; and map the filled surface back to the three corresponding faces of the data-cube.

Embodiments described with respect to one aspect of the invention may be, applied to another aspect of the invention (e.g., features of embodiments described with respect to one independent claim are contemplated to be applicable to other embodiments of other independent claims).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, aspects, features, and advantages of the invention will become more apparent and may be better understood by referring to the following description taken in conjunction with the accompanying drawings, in which:

FIG. 13A-13D are example images illustrating results of 2-D slice-by-slice stereology operations performed automatically on a 3D image of a mouse tibia following central axis determination, according to an illustrative embodiment of the present disclosure.

DETAILED DESCRIPTION

Figure 1:
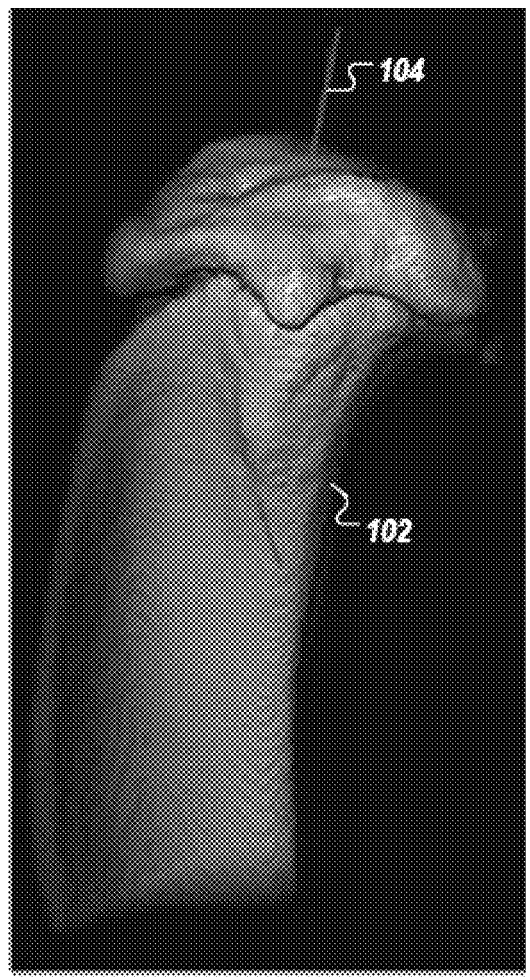
FIG. 1 is an image illustrating the principal axes of the tibia of a mouse imaged by a microCT scanner.

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, "extracting" or "extraction" of bone axes refers to the detection, segmentation, calculation, visualization, and the like, of axes (e.g., central axes) of bones.

As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation.

As used herein, "long bone" means a bone of an extremity (e.g., of a mammal, e.g., mouse, rat, etc.) that has a length greater than the width (e.g., femur bone). In some embodiments, a long bone is a bone of the legs, the arms, the hands, the feet, the fingers, the toes, or collar bones. In some embodiments, a long bone is selected from the following: femora, tibiae, fibulae, humeri, radii, ulnae, metacarpals, metatarsals, phalanges, and clavicles (e.g., of collar bones). Certain embodiments described herein apply to either long bones or non-long bones, including, for example, short bones, flat bones, sesamoid bones, and irregular bones. In certain embodiments, non-long bones include bones with partially circular shapes, e.g., the pelvic girdle.

As used herein, a "mask" is a graphical pattern that identifies a 2-D or 3-D region and is used to control the elimination or retention of portions of an image or other graphical pattern.

Described herein are systems and methods for automated detection of bone central axes from in vivo or ex vivo images (e.g., 3-D images). In some example embodiments, the 3-D image is an in vivo image of an animal subject (e.g., a mammal such as a mouse). In some embodiments, the 3-D image is an ex vivo image of a sample (e.g., bone sample) from an animal subject (e.g., a mammal such as a mouse). In some embodiments, images can be acquired and/or processed by medical imaging devices such as CT scanners, microCT scanners, and the like. It should be understood that an image, such as a 3-D image, may be a single image or a set or series of multiple images.

Figure 3:
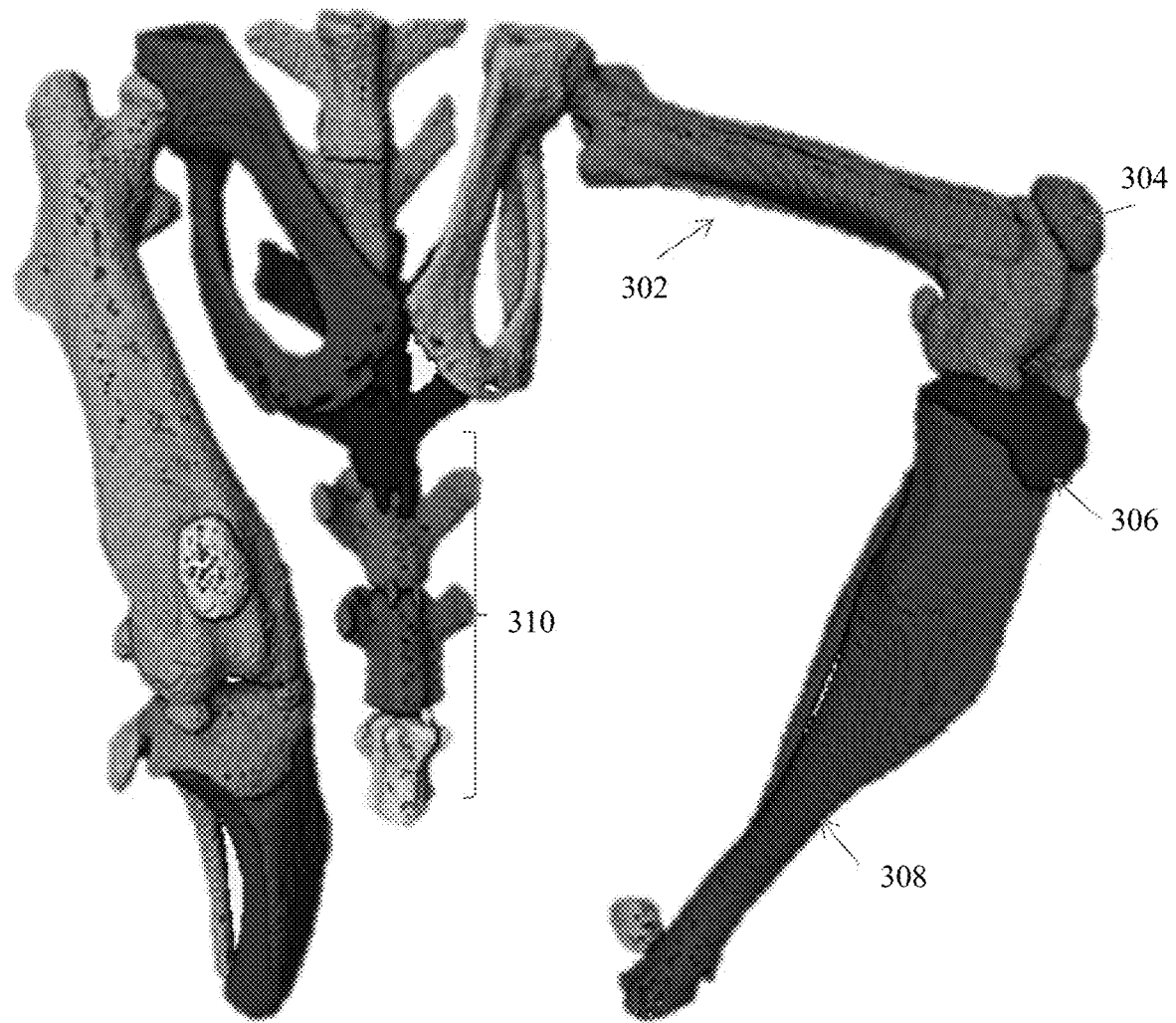
FIG. 3 is an image showing a 3-D representation of the bones of the hind limb of a mouse imaged by a microCT scanner segmented using splitting filters, according to an illustrative embodiment of the present disclosure.

Central axes of bones can effectively encapsulate characteristics and data of bones, including, for example, spatial features, direction, orientation, and shape of a bone. Using bone detection and segmentation algorithms, the skeletal bones of animal subjects (e.g., scanned by CT or microCT scanners) are detected, segmented, and visualized, as shown in FIG. 3. When visualizing a collection of bones, the bone axes effectively represent the orientation of the bones relative to each other. The bone axes are also useful for determining bone directions (e.g., during computer-based analysis), as the axes carry quantitative structural information such as the spatial angle of the bone orientation. Importantly, the 2-D planes perpendicular to the central axes are used for slice-by-slice stereology analysis of bones. By moving along the central axis and extracting 2-D planes normal to the central axis, 2-D slice-by-slice analyses such as stereology can be carried out as shown in FIG. 13 A-D, described in more detail below.

Some example embodiments described herein relate to calculating and extracting central axes of skeletal bones to capture both the general and localized tangential directions of the bones. The calculation of central axes also identifies, among other things, the shape, form, and curvature of the bones. That is, the central axis represents a medial path that describes, among other things, the main center-line, shape, and orientation of a bone.

Figure 2:
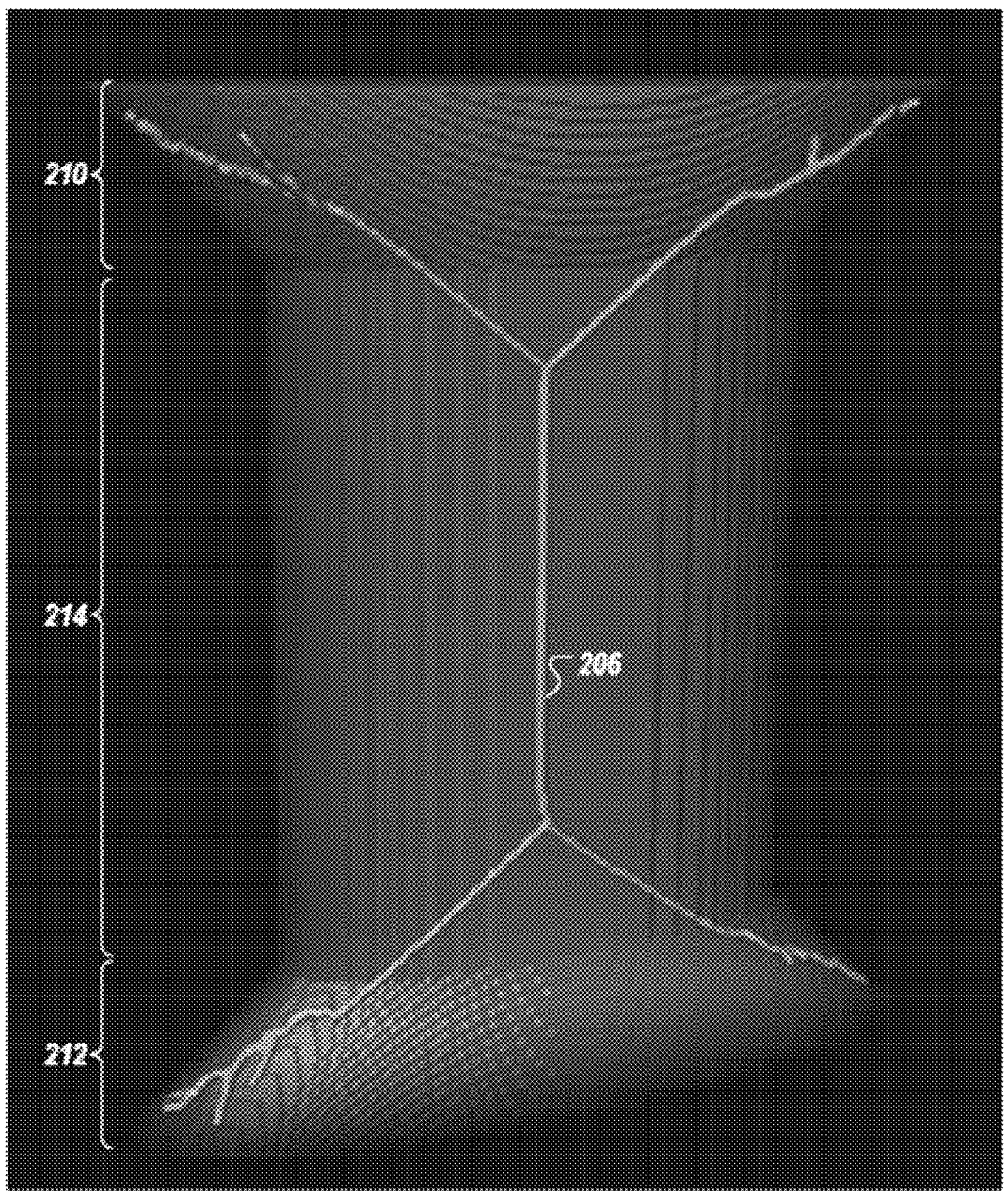
FIG. 2 is an image illustrating an automated 3D skeletonization of an elliptical prism annexed by conical sections on top and bottom.

Description and calculation of bone central axes is challenging because bones are not homogeneous solid objects with simple regular shapes; they can take arbitrary shapes and include hollow regions and holes with various densities and porosities. In addition, morphological skeletons of binary bone masks, which reduce 3D regions into line sets, may not be represented by a single-branched axis, but rather, they may include multiple branches, especially at the distal ends, confounding traditional analysis. Thus, in certain embodiments, mere 3D skeletonization of a binary bone mask, or even a filled bone mask, is found to be insufficient for extracting a central axis. As shown in FIG. 2, skeletonization of solid objects results in multi-branched trees or graphs which cannot serve as a medial or central axis. Peripheral branches of skeletons only reflect certain regional spatial attributes of the solid object. 3D skeletonization reduces a solid object into a set of curved lines, only some of which carry information useful for calculation of the solid object's central axis; thus, in certain embodiments, further steps, as described herein, may be performed to extract the central axis of a solid object from its morphological skeleton in an accurate, automated, and reproducible way.

In certain embodiments, bone central axes are extracted from morphological skeletons. Skeletons are generally defined for filled 2-D or 3-D binary objects. In some embodiments, a skeleton may be represented and/or illustrated as a skeletal tree. In some embodiments, in filled 3-D objects, the morphological skeleton is extracted by performing iterative thinning on the 3-D object binary mask. The process of extracting the morphological skeleton is referred to as skeletonization. In some embodiments, skeletonization involves extracting the locus of the center of all maximally inscribed spheres in a 3-D object. Referring to FIG. 2, the result of direct skeletonization of an elliptical prism annexed by conical sections is displayed. For 3-D objects elongated in a certain direction, the skeleton is often comprised of a main branch that extends through the object, and a few minor branches that extend from the main branch to the boundary of the object, similar to the skeleton shown in FIG. 2.

Results of direct 3-D skeletonization of bones are often not useful candidates for the central axis calculation and extraction due to two primary reasons. First, a skeletal bone is almost never a homogenously filled 3-D object, and its inner compartment (e.g., the trabeculae), is a porous structure distributed over the marrow. A direct 3-D skeletonization of the bone mask (without undergoing filling operations) would represent the medial tree spanning the cortical shell and trabecular network of the bone, rather than the morphological skeleton of the bone in its entirety including the cortical, trabecular, and marrow compartments. Second, because of peripheral branches (e.g., multi-branched segments extending into the conical sections 210, 212), the skeleton, in its raw form, is not a single-branched central axis that represents the orientation and form of a 3-D object. The peripheral branches of the 3-D skeleton only carry localized structural information especially at the distal ends and are not useful in guiding and automating slice-by-slice measurements.

FIG. 3 shows a 3-D image comprising multiple bones of a mammal, according to an exemplary embodiment. More specifically, FIG. 3 illustrates bones of the hind limb of a mouse (e.g., imaged by a microCT scanner) that are segmented into a femur, tibia, and patella, using splitting filters.

In FIG. 3, the bones 302, 304, 306, 308 have been morphologically isolated and/or segmented from one another. Other bones have also been isolated, including the individual vertebrae 310. Various common approaches may be taken toward isolating and/or segmenting the individual bones of the 3-D image, as shown in FIG. 3, for example, the systems and methods described in U.S. patent application Ser. No. 14/812,483, filed Jul. 29, 2015, entitled, "Systems and Methods for Automated Segmentation of Individual Skeletal Bones in 3D Anatomical Images," the text of which is incorporated herein by reference in its entirety. In certain embodiments, isolation and/or segmentation employs linear classification or regression, and a signal to noise ratio (S/N) corresponding to one or more features may be used to measure quality of classification or regression. In certain embodiments, constraints for classification or regression are chosen empirically. For example, in some embodiments, constraints for classification or regression are chosen by running the same set of examples several times with varying constraints. Appropriate constraints may be chosen to strike a balance between accuracy and computing time in the isolation and/or segmentation algorithm chosen.

Figure 4:
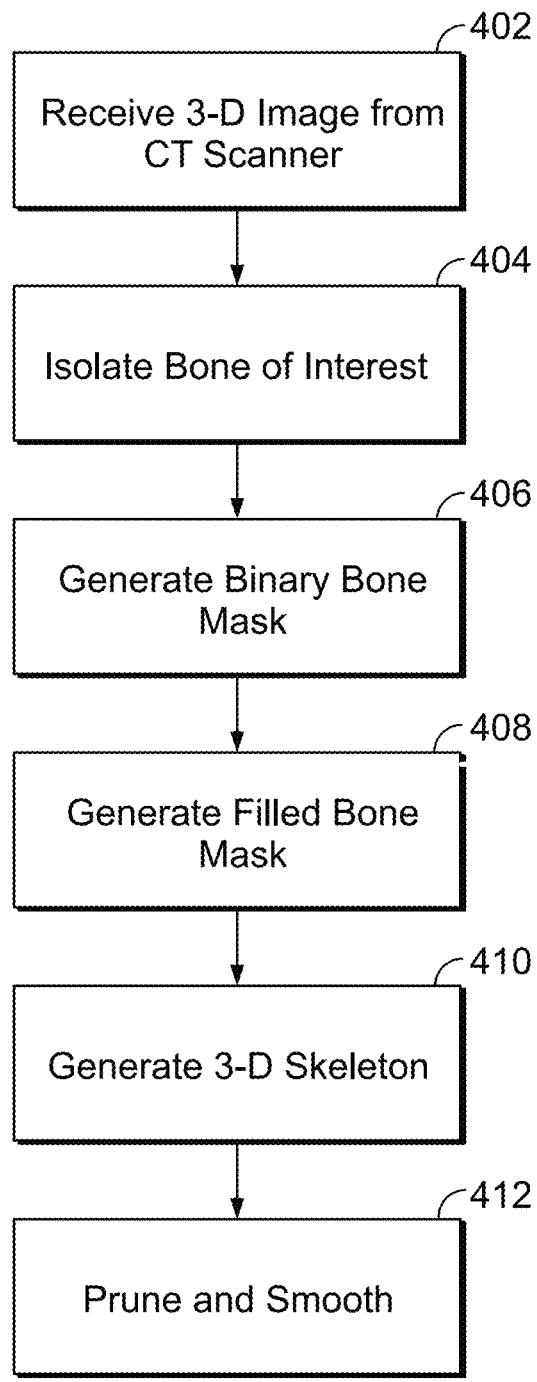
FIG. 4 is a flow chart showing a method of automated characterization and calculation of a central bone axis, according to an illustrative embodiment of the present disclosure.

FIG. 4 illustrates a flow chart for extracting a central bone axis from an isolated binary bone mask, according to an exemplary embodiment. Prior to identifying (e.g., extracting) the central axis of the bone, a 3-D image (or a series of 3-D images) of the bones of a mammal is received, for example, from a CT or micro-CT scanner [402]. The bone (from which the axis is to be calculated) is morphologically isolated and/or segmented from a collection of bones [404], so that only the bone of interest (e.g., long bone) is analyzed. Morphological isolation and/or segmentation is described above in further detail with reference to FIG. 3.

After morphological isolation, the 3-D image of the bone(s) is converted to a binary bone mask [406]. In several embodiments, a 3-D binary bone mask is a three-dimensional array comprising voxels in an included (e.g., binary true) or excluded (e.g., binary false) state. A voxel in the binary true state in the mask corresponds to a region containing bone tissue in the 3-D image of the bone(s). Conversely, a voxel in a binary false state in the mask corresponds to an empty or non-bone tissue in the 3-D image. As such, in certain embodiments, the binary bone mask represents at least the cortical and trabecular compartments of the bone(s). In further embodiments, the binary bone mask is initially filled (e.g., the interior portion contents such as marrow) by binary true voxels (e.g., the binary bone mask represents a solid 3D bone volume composed of cortical, trabecular, and marrow compartments). An example technique for generating a binary bone mask is further described in detail in U.S. patent application Ser. No. 14/162,693 filed Jan. 23, 2014, which is incorporated herein by reference in its entirety.

Figure 6:
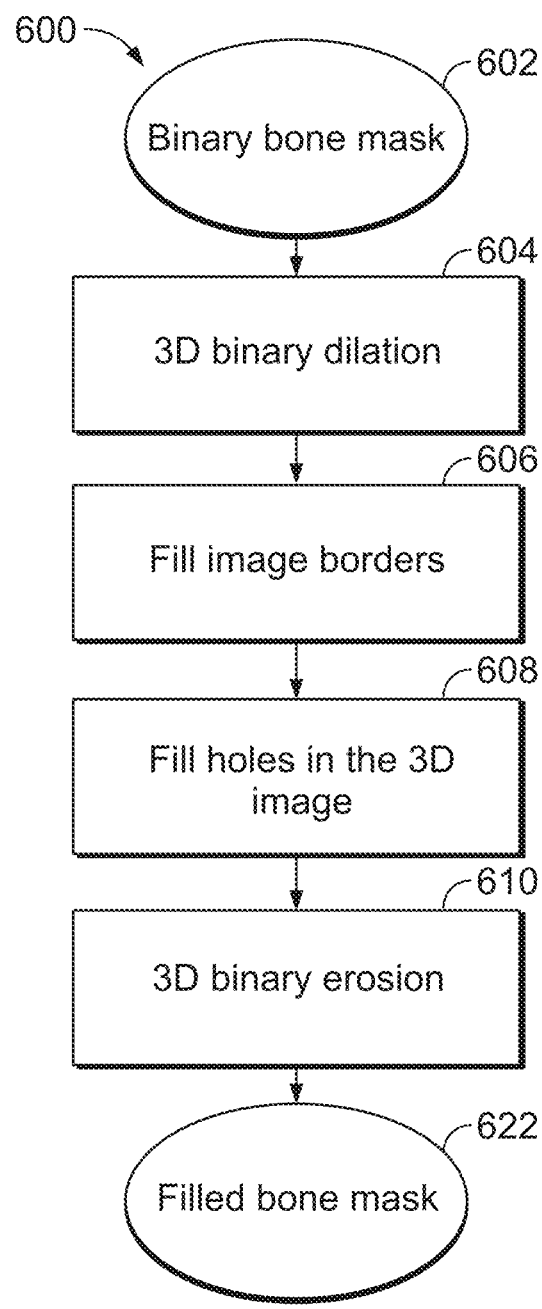
FIG. 6 is a flow chart showing a morphological bone filling method, according to an illustrative embodiment of the present disclosure.

In certain embodiments, the binary mask of the bone is filled by morphological processing [408], which is described in further detail in the flowchart depicted in FIG. 6. In certain embodiments, filling a 3-D object (e.g., a binary bone mask) generally refers to the process of identifying the internal voxels (e.g., the internal sub-volume bounded by the surface) of the object and adding all of them to the binary bone mask (e.g., by changing their states to binary true). In some embodiments, skeletonization is performed on the filled bone by iterative 3-D thinning [410], which is described in detail below. In some embodiments, the skeleton is pruned (e.g., minor branches are removed) down to a single branch (e.g., the trunk) and smoothed [412], an illustrative method for which is described in detail in the flowchart depicted in FIG. 11. In certain embodiments, these three steps (408, 410, and 412) yield a single-branched curve that follows the medial path of the bone, effectively identifying and isolating the central axis of the bone.

Figure 5:
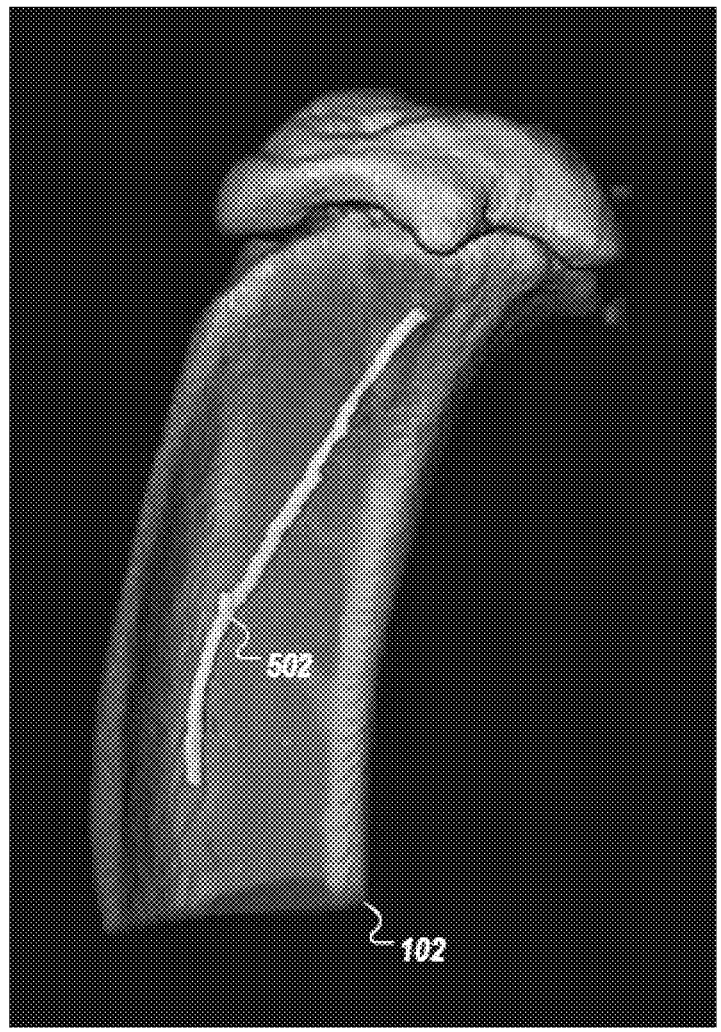
FIG. 5 is an image illustrating a central axis of a tibia of a mouse imaged by a microCT scanner, according to an illustrative embodiment of the present disclosure.

Referring to FIG. 5, the result of the central bone axis identification method described in reference to FIG. 4 is shown. The central bone axis 502 is obtained after the steps outlined in FIG. 4 are carried out, including pruning and smoothing the 3D morphological skeleton of the filled binary bone mask.

FIG. 6 is a flowchart of a process for filling a binary mask of a bone (e.g., bone filling) using morphological processing, according to an exemplary embodiment. Bone filling is a step in extracting the central axis of a bone, e.g., step 408 of the method depicted in FIG. 4. For example, in certain embodiments, bone filling is performed by adding the internal compartment (e.g., marrow) of the bone to the bone mask. The presence of cracks or veins in the bone shell that connect the internal part or marrow of the bone to the background of the bone mask make bone filling more challenging. Because of the veins and/or cracks in the bone shell, the internal compartment is morphologically connected to the background, and additional steps are required for accurate, robust detection of the internal compartment of the bone. For example, in some embodiments, the internal compartment is detected by performing a binary subtraction (e.g., an AND NOT operation) between dilated masks of the bone before and after morphological filling. In certain embodiments, dilation refers to expansion of an image, proportionately or disproportionately, along any axis or direction. In some embodiments, the dilation is 3-D spherical dilation performed using a spherical structuring element of a size ranging from 3-5. Various methods of dilation may be employed. Further discussion of dilation and related operations are discussed in International Application PCT/IB2011/002757, filed Sep. 12, 2011, published as International Patent Application Publication No. WO/2013/038225, which is incorporated herein by reference in its entirety. In some embodiments, the internal compartment of the bone is obtained by dilating the result of this subtraction. In some embodiments, border filling in the bone filling process is performed by applying 2-D filling to the border planes of the data-cube containing the bone image stack, as outlined in detail in the flowchart of FIG. 8.

Still with reference to FIG. 6, a binary bone mask is generated [602] (e.g., retrieved) from a medical image such as a CT or a microCT scan of one or more bones of a mammal. In certain embodiments, the various bones contained in the image are automatically isolated and/or segmented (see FIG. 3). For illustrative purposes, the binary bone mask generated in step 602 is herein referred to as Image0, although the method does not rely on any particular name being assigned to any image. In turn, the binary bone mask (Image0) is dilated, by a spherical structuring element, e.g., of size 3-10 depending on the metric voxel dimensions of the image, and the dilated binary bone mask is stored as Image1 [604].

The borders of Image1 are then identified and filled [606]. Morphological holes (e.g., gaps and/or discontinuities) are also filled [608]. Border filling is described in more detail below with reference to FIG. 8. Then, 3D binary erosion is performed [610] to produce the filled bone mask [622].

In certain embodiments, the result of the 3D hole filling and border filling operations is stored as Image2. Image1 is then subtracted from Image2 [610], resulting in a mask effectively representing the location of filled holes and cracks. In certain embodiments, small spots, defined as connected components with volumes smaller than empirically determined bounds, are removed from the resulting mask and the image is again dilated, and stored as Image3. In turn, a new image is generated by combining Image0 with Image3, resulting in the binary bone mask of Image0 superimposed with the filled holes represented by Image3. The borders of the resulting image (Image0+Image3) are filled and subsequently the holes of the 3D image are filled. The holes are identified as the empty or binary false voxels located in the internal compartment of the dilated bone mask (morphologically disconnected from the background image by the dilated bone mask). The holes are filled by being added to the bone mask (or their voxel values being updated to 1 or binary true).

Figure 7A:
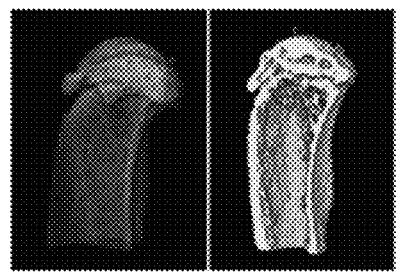
FIGS. 7A-7E are example images created following steps of the morphological bone filling method of FIG. 6, according to an illustrative embodiment of the present disclosure.
Figure 7B:
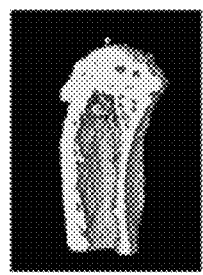
Figure 7C:
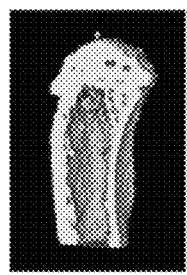
Figure 7D:
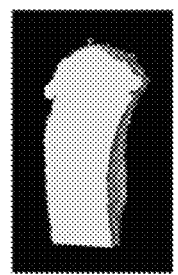
Figure 7E:
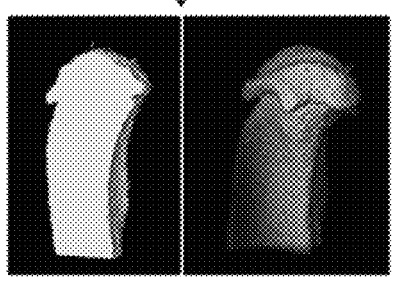

FIGS. 7A-7E show the results of the steps described in reference to FIG. 6. FIG. 7A depicts two views—external and cut-away—of the result of the binary bone mask, step 602 of the method of FIG. 6. FIG. 7B depicts the result of 3D binary dilation, step 604 of the method of FIG. 6. FIG. 7C depicts the result of border filling operations, step 606 of the method of FIG. 6. FIG. 7D depicts the result of morphological hole filling, step 608 of the method of FIG. 6. FIG. 7E depicts the filled bone mask resulting from 3D binary erosion, step 610 of the method of FIG. 6.

Figure 8:
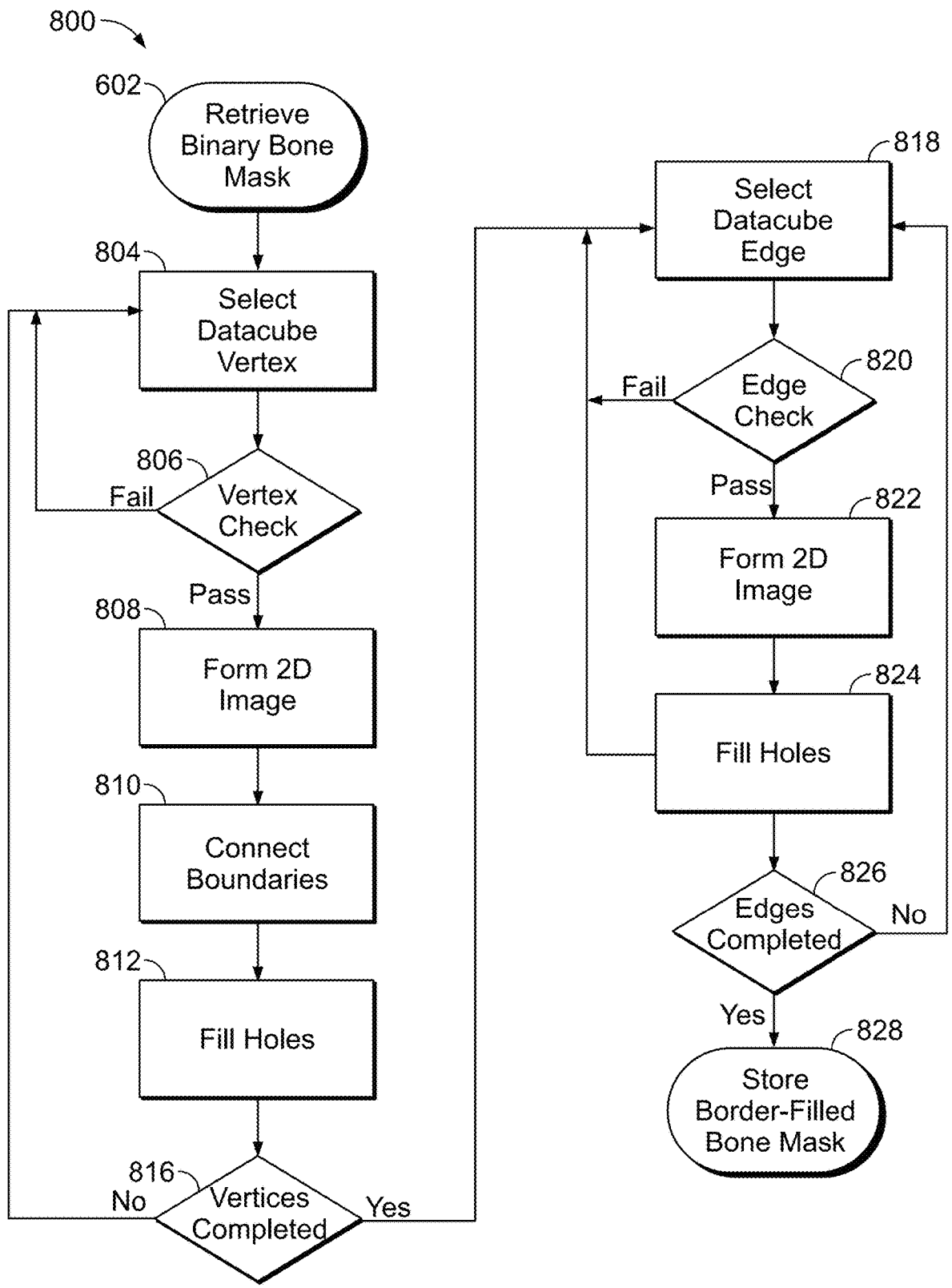
FIG. 8 is a flow chart showing a border filling method on a 3D binary bone image (data-cube), according to an illustrative embodiment of the present disclosure.

FIG. 8 illustrates a process for performing border filling, according to an exemplary embodiment. In some example embodiments, border filling is performed during the process of generating a binary bone mask (e.g., FIG. 6). Border filling is performed on an unprocessed or processed bone mask (e.g., a dilated bone image resulting from step 604 of FIG. 6).

Figure 9A:
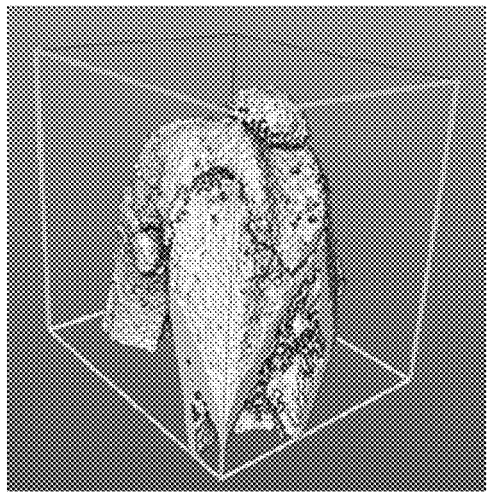
FIGS. 9A-9F are example images created following steps of the border filling method of FIG. 8, according to an illustrative embodiment of the present disclosure.
Figure 9B:
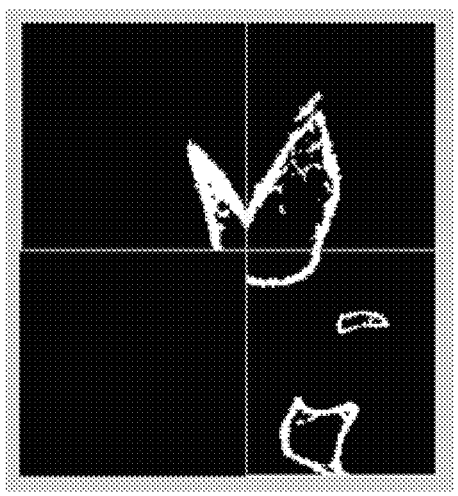
Figure 9C:
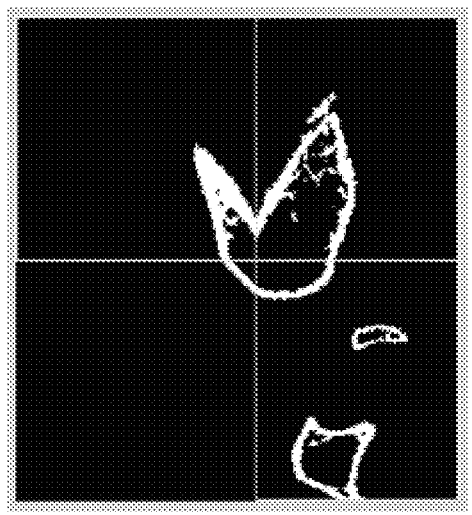
Figure 9D:
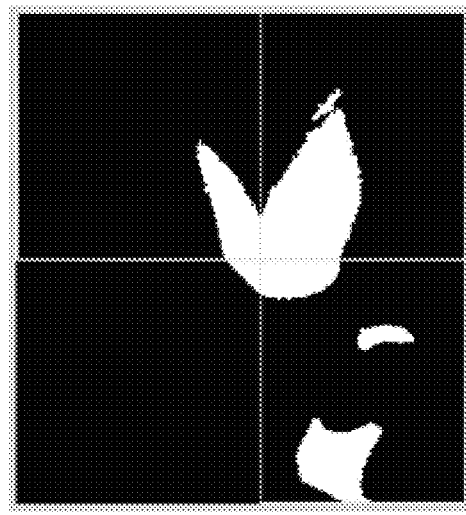
Figure 9E:
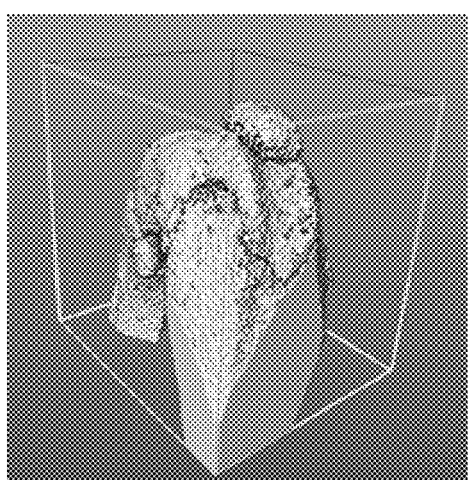
Figure 9F:
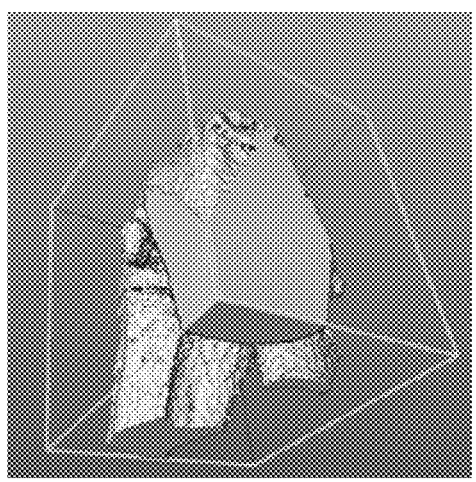

More specifically, to initiate border filling, the binary bone mask used in the exemplary embodiment of FIG. 6 is retrieved [602]. In some embodiments, image data (e.g., of the binary bone mask) is represented digitally as one or more data-cubes. In various embodiments, a data-cube comprises a 3D array of values corresponding to voxels in the 3-D bone mask including twelve edges and eight vertices, each of the vertices being associated with three edges. Each edge of the data-cube is associated with two faces. A first data-cube vertex is selected from the eight vertices [804], an example of which is shown in FIG. 9A. The selected vertex is checked to ensure all three edges connected to the vertex contain voxels belonging to the binary mask [806]. If an edge connected to a vertex contains a binary mask voxel, it is associated with and/or assigned a true (e.g., binary true) state. If all of the edges connected to the selected vertex are associated with true voxels, the vertex check is satisfied. Otherwise, if the vertex check does not pass, the next vertex is selected. If the vertex passes the voxel check, a 2-D image is formed by concatenating the three faces connected to the vertex with an all-zero face as a quadrant [808], an example of which is shown in FIG. 9B. Pixels with binary true values bordering the all-zero quadrant are then connected diagonally by updating the values of the corresponding pixels of the all-zero quadrant to binary true [810], as depicted in FIG. 9C. Morphological holes in the resulting concatenated 2-D image are then filled and the filled surfaces are mapped back to the three corresponding faces of the data-cube [812], as depicted in FIG. 9D (2-D image) and FIGS. 9E and 9F (two views of the resulting data-cube).

If all of the vertices have been checked and processed (e.g., completed) [816], the method proceeds to step 818. Otherwise, the method returns to select the next vertex in the data-cube, in step 804. With all vertices completed, a first data-cube edge is selected [818]. The edge is checked to ensure both of the faces connected to the edge and the edge itself contain binary true voxels [820]. If the edge check is passed (e.g., edge is associated with true voxels), a 2-D image is formed from concatenating the two faces connected to edge [822]. Otherwise the next data-cube edge is selected as in step 818. Morphological holes in the 2-D image are filled and the filled surfaces are mapped back to the two corresponding faces of the data cube [824]. If all edges have been completed [826], the method continues to step 828, otherwise the next edge is selected. After all edges are completed, the holes on each individual face of the data-cube are filled [830], thereby generating a border-filled bone mask. The border-filled bone mask is stored in memory [828].

As mentioned above, identifying a central bone axis also includes a step of 3-D thinning. The concept of 3-D thinning is described in more detail in Building Skeleton Models via 3-D medial Surface/Axis Thinning Algorithms (Lee, T. C., Graphical Models and Image Processing, Vol. 56, No. 6, November, pp. 462-478, 1994), which is incorporated herein by reference in its entirety.

Generally, 3-D thinning shrinks or reduces solid objects, areas, or volumes, such as a filled 3-D object (e.g., bone) to a morphological skeleton (see FIG. 10), with major and minor branches. In some embodiments, the skeleton (or the medial surface) of a structure is the locus of the center of all maximally inscribed spheres of the object in 3-D space (e.g., Euclidean space) where each of the spheres touch the boundary at more than one point. In some embodiments, a distance transformation is used to thin the 3-D image. In some embodiments, border points are repetitively deleted under topological and geometrical constraints until a smaller set of connected points is acquired. In some embodiments, the 3-D skeleton substantially represents or is an approximation of the "true" skeleton in the 3-D Euclidean space. In some embodiments, level set marching approaches are performed.

More specifically, the iterative deletion of border points provides 3-D thinning while maintaining topological properties of the image being thinned. In some embodiments, each thinning iteration is divided into subcycles according to the type of border point (e.g., north, south, west, east, up, bottom). The border points that are deleted are restricted based on topological and geometric constraints, for example, to avoid undesired object separation or elimination in the image. In some implementations, medial surface thinning (MST) and/or medial axis thinning (MAT) may be used as geometric constraints of the border deletion process of a 3-D thinning operation. That is, MST is used to identify surface points that are not deleted during thinning. That is, medial surface thinning identifies surfaces that are approximately located to a center line. MAT differs from MST in that the extracted skeleton consists of arcs and/or curves instead of surfaces that approximate the center line. MST and MAT are both described in further detail in Building Skeleton Models via 3-D medial Surface/Axis Thinning Algorithms (Lee, T. C., Graphical Models and Image Processing, Vol. 56, No. 6, November, pp. 462-478, 1994), which is incorporated herein by reference in its entirety.

Figure 10:
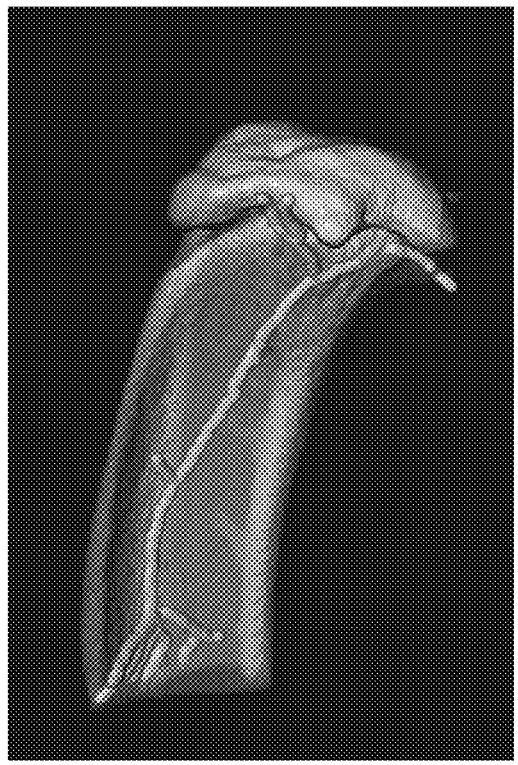
FIG. 10 is an image illustrating a skeleton of the tibia of a mouse imaged by microCT scanner; the image was computed using iterative 3-D thinning on the filled bone, according to an illustrative embodiment of the present disclosure.

FIG. 10 shows a 3-D skeletonization of a filled bone mask from the tibia of a mouse, according to an exemplary embodiment. The skeleton 902 may be further pruned and smoothed, as shown below with reference to FIG. 11.

Figure 11:
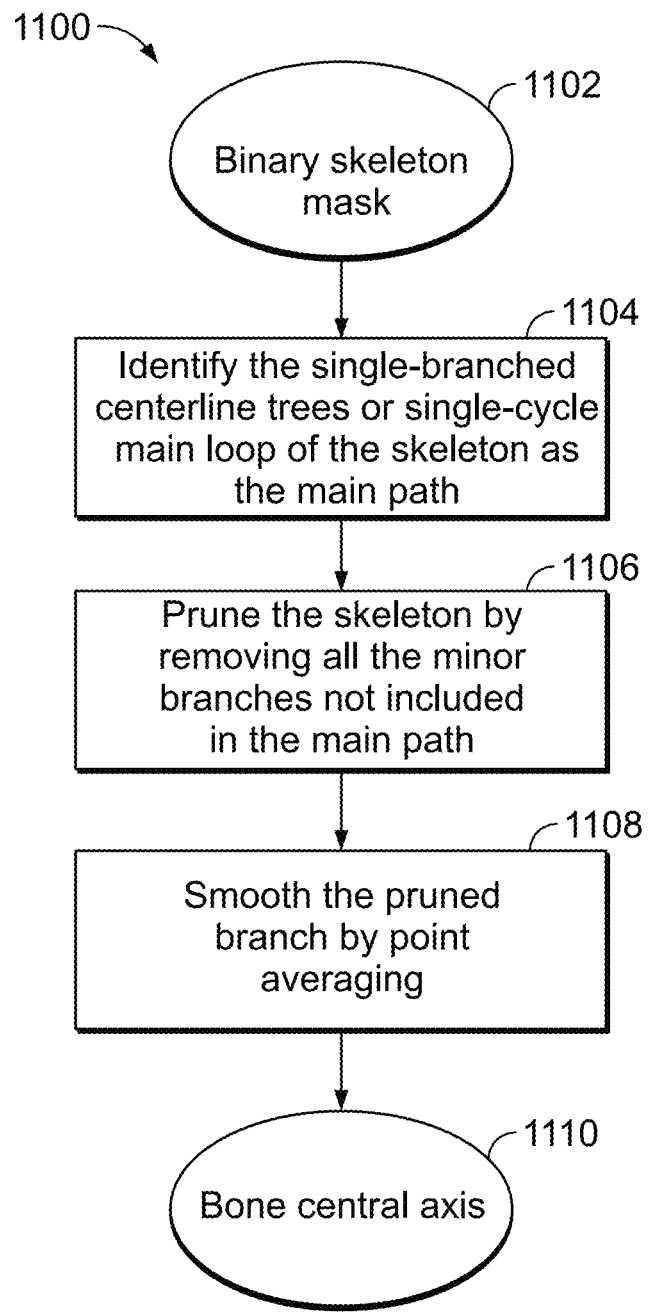
FIG. 11 is a flow chart showing a method for pruning and smoothing of the morphological skeleton of a bone, according to an illustrative embodiment of the present disclosure.
Figure 12A:
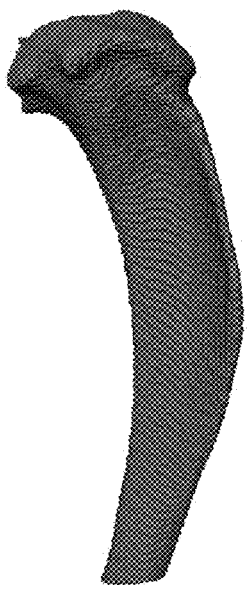
FIG. 12A-12H are images created following steps of the pruning and smoothing method of FIG. 11 applied to 3D image of a mouse tibia, according to an illustrative embodiment of the present disclosure.
Figure 12B:
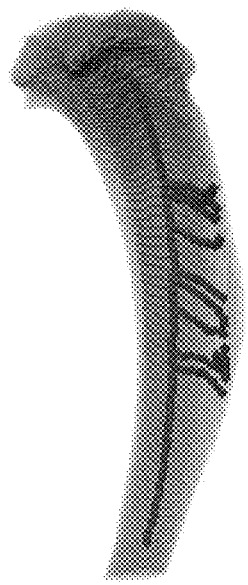
Figure 12C:
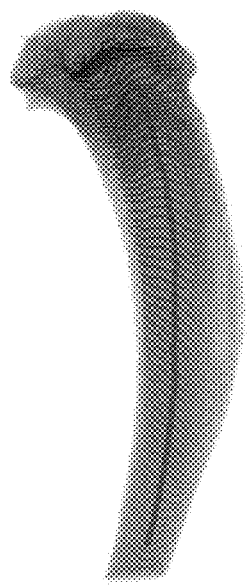
Figure 12D:
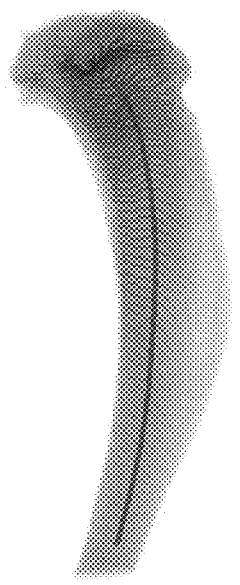
Figure 12E:
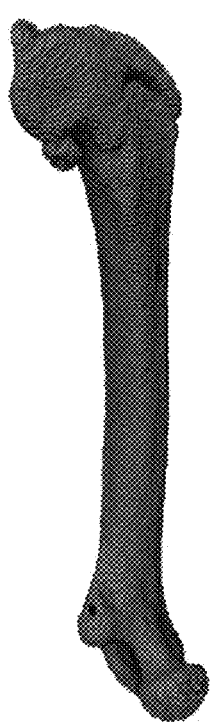
Figure 12F:
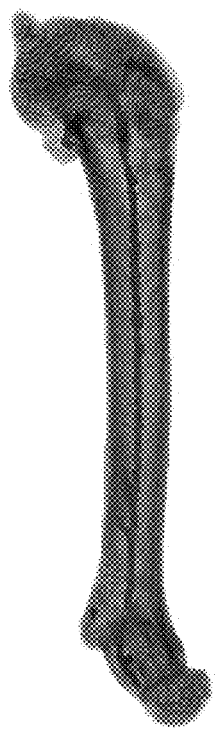
Figure 12G:
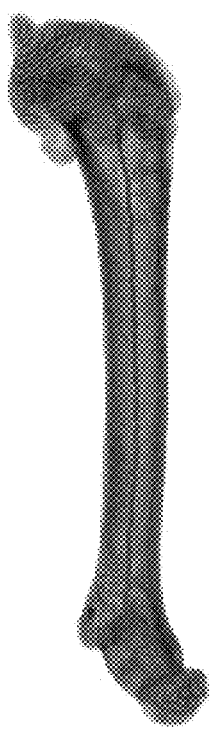
Figure 12H:
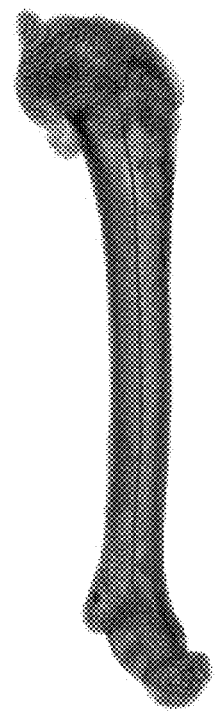

FIG. 11 illustrates a process [1100] of pruning and smoothing a skeleton to yield the central axis of the bone, according to an exemplary embodiment. First a binary skeleton mask is retrieved [1102]. Subsequently, a particular path (e.g., a main or central path) in the skeleton is identified [1104], e.g., by finding (i) the centerline tree of the skeleton (for example, via the method described in "TEASAR: tree-structure extraction algorithm for accurate and robust skeletons Sato, M.; Bitter, I.; Bender, M. A.; Kaufman, A. E.; Nakajima, M. Computer Graphics and Applications, 2000. Proceedings. The Eighth Pacific Conference on Volume, Issue, 2000 Page(s):281-449") or (ii) a single-cycle main loop of the skeleton, depending on whether the bone morphological skeleton has a tree structure with no loops (e.g., long bones such as femur) which is often the case for mammalian bones, or the bone morphological skeleton has loops (e.g., pelvic girdle). In certain embodiments, the centerline tree of the skeleton is found using the TEASAR algorithm referenced above, which includes (1) reading binary segmented voxels inside the object; (2) cropping the volume to just the object; (3) computing the distance from boundary field (DBF); (4) computing the distance from any voxel field (DAF); (5) computing the penalized distance from root voxel field (PDRF); (6) finding the farthest PDRF voxel labeled as inside; (7) extracting the shortest path from that voxel to the root; (8) labeling all the voxels near the path as 'used to be inside'; and (9) repeating steps 6 to 8 until no inside voxels remain.

In the pruning step [1106], the minor branches of the skeleton are removed from the identified main path, thus reducing the skeleton to a single branch. To prevent the irregular shapes of the distal ends of bones from affecting the central axis determination, the pruned branch is further smoothed by point averaging [1108]. The end result of this step is the bone central axis [1110], an example of which is illustrated in FIG. 5 at reference [502].

FIG. 12A-12H are images created following steps of the pruning and smoothing method of FIG. 11, as applied to the tibia (FIGS. 12A-12D) and femur (FIGS. 12E-12H) of a mouse scanned by a microCT imaging platform after bone segmentation as shown in FIG. 3. From left to right, the images show the bone mask (FIGS. 12A/12E), the result of the skeletonization step [1104] (FIGS. 12B/12F), the result of the pruning step [1106] (FIGS. 12C/12G), and the result of the smoothing step [1108] (FIGS. 12D/12H), thereby producing the central axis for the tibia and femur.

In some implementations, the identified central axis of the bone is used to quantify structural characteristics (e.g., features) of the bone, such as the bone's shape, form, localized tangential directions, curvature, and the like. These characteristics may be used, in turn, to characterize the bone, for example, by identifying abnormalities, identifying the bone as a specific bone, and the like. In some implementations, the identified central axis is used to render images of the bone or the set of bones with which the bone is associated. It should be understood that the characteristics of a bone, identified using the bone's central axis, can be used, for example, for other imaging (e.g., rendering), diagnostics, and therapeutic purposes, as well as for other applications.

For example, in certain embodiments, the identified central axis of the bone is used for stereological measurements and slice-by-slice studies of the bone. FIG. 13A-13D are example images illustrating results of 2-D slice-by-slice stereology operations performed accurately and automatically following central axis determination. The planes perpendicular to the central axis are used to create 2-D image slices of the bone cross-section. Parameters such as average cortical thickness can then be calculated from these 2-D slices automatically. For example, FIG. 13A shows a mouse tibia 1300 following determination of the bone central axis per methods described herein. Planes 1302, 1306, and 1310 are identified. These planes are perpendicular to the central axis at various locations along the length of the bone. Images of 2-D cross-sections at these planes are obtained, e.g., images of FIGS. 13B-13D. FIG. 13B corresponds to plane 1302, FIG. 13C corresponds to plane 1306, and FIG. 13D corresponds to plane 1310. From the 2-D cross-sections, various bone properties can be determined, for example, average cortical (shell) thickness. Any number of cross-sections may be taken. In the case shown in FIG. 13, the average cortical thickness was automatically determined to be 3.98 voxels or 198 microns. The method disclosed herein provides an automated, robust way of obtaining this information directly from a scan (e.g., micro-CT scan), thereby eliminating operator error and variability due to "by hand" measurements.

As discussed above, certain embodiments of the procedures described herein relate to extracting the central axis of a bone to guide stereological measurements or capture, for example, of the direction, overall shape, and spatial characteristics of the bone. Various other embodiments utilize the image processing methods described herein, including procedures such as border filling, bone filling, and pruning/smoothing, for other applications. For example, the image processing methods described herein may be used in bone segmentation/separation using morphological separation approaches such as watershed. In some embodiments, the morphological separation is performed on filled bones rather than the original bone masks. Moreover, border and bone filling are also useful in segmenting the cortical and trabecular compartment of a bone, for example.

Figure 14:
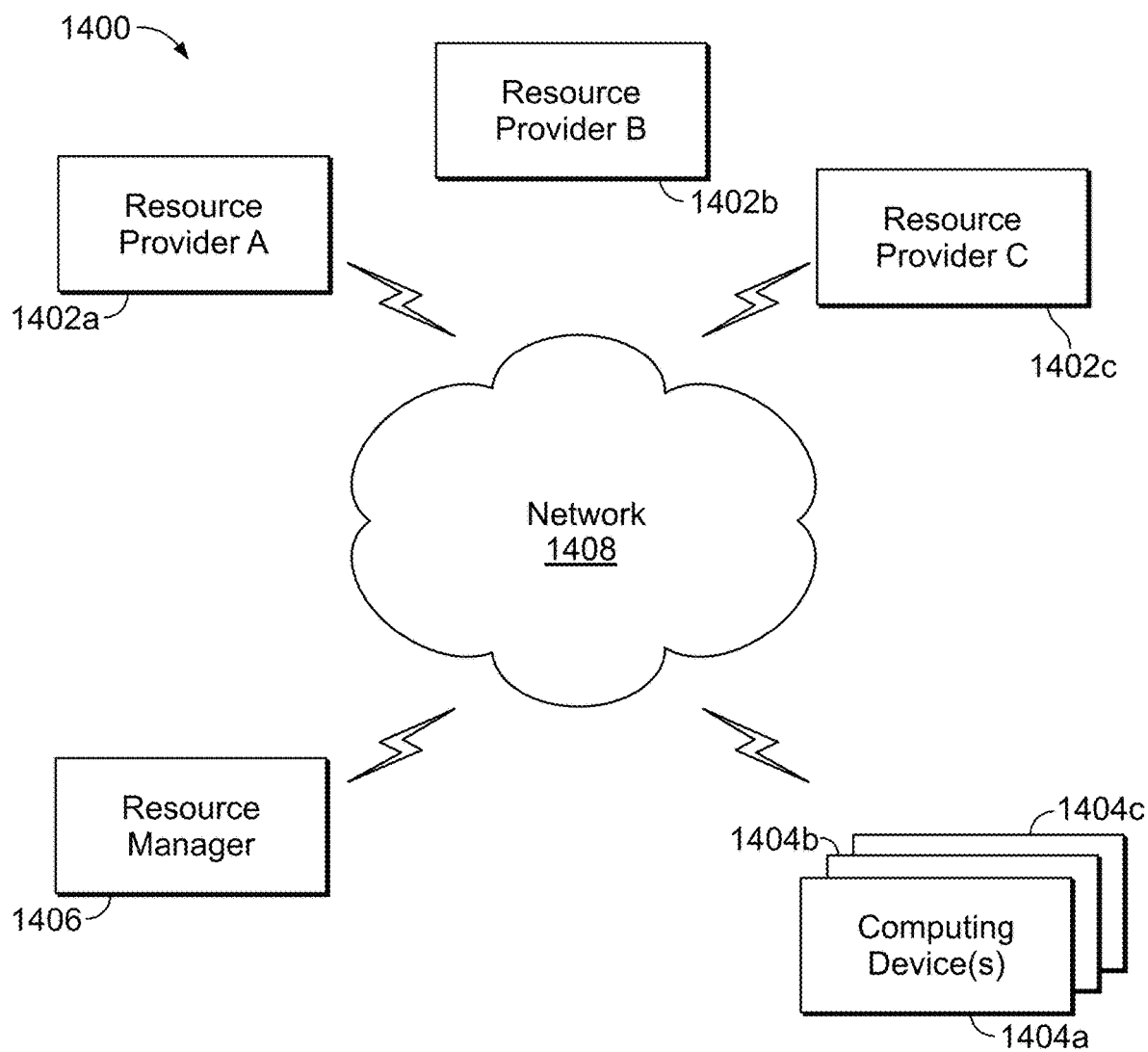
FIG. 14 is a block diagram of an example computing device and an example mobile computing device, for use in illustrative embodiments of the present disclosure.

FIG. 14 shows an illustrative network environment 1400 for use in the methods and systems described herein. In brief overview, referring now to FIG. 14, a block diagram of an exemplary cloud computing environment 1400 is shown and described. The cloud computing environment 1400 may include one or more resource providers 1402a, 1402b, 1402c (collectively, 1402). Each resource provider 1402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1402 may be connected to any other resource provider 1402 in the cloud computing environment 1400. In some implementations, the resource providers 1402 may be connected over a computer network 1408. Each resource provider 1402 may be connected to one or more computing device 1404a, 1404b, 1404c (collectively, 1404), over the computer network 1408.

The cloud computing environment 1400 may include a resource manager 1406. The resource manager 1406 may be connected to the resource providers 1402 and the computing devices 1404 over the computer network 1408. In some implementations, the resource manager 1406 may facilitate the provision of computing resources by one or more resource providers 1402 to one or more computing devices 1404. The resource manager 1406 may receive a request for a computing resource from a particular computing device 1404. The resource manager 1406 may identify one or more resource providers 1402 capable of providing the computing resource requested by the computing device 1404. The resource manager 1406 may select a resource provider 1402 to provide the computing resource. The resource manager

1406 may facilitate a connection between the resource provider 1402 and a particular computing device 1404. In some implementations, the resource manager 1406 may establish a connection between a particular resource provider 1402 and a particular computing device 1404. In some implementations, the resource manager 1406 may redirect a particular computing device 1404 to a particular resource provider 1402 with the requested computing resource.

Figure 15:
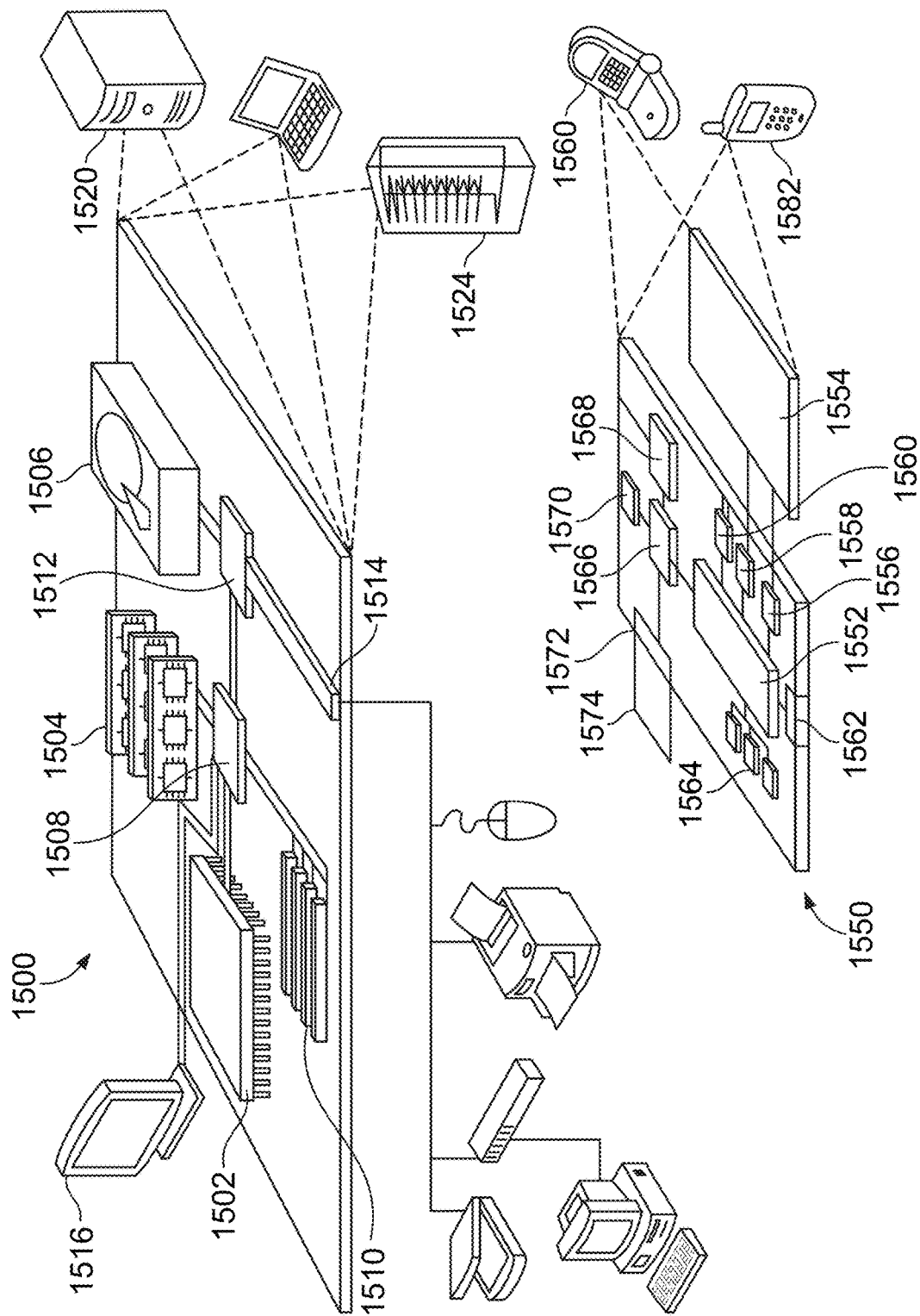
FIG. 15 is a block diagram of an example computing environment, for use in illustrative embodiments of the present disclosure.

FIG. 15 shows an example of a computing device 1500 and a mobile computing device 1550 that can be used in the methods and systems described in this disclosure. The computing device 1500 is intended to represent various forms of digital computers, such as laptops, desktops, workstations, personal digital assistants, servers, blade servers, mainframes, and other appropriate computers. The mobile computing device 1550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and may be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1504 stores information within the computing device 1500. In some implementations, the memory 1504 is a volatile memory unit or units. In some implementations, the memory 1504 is a non-volatile memory unit or units. The memory 1504 may also be another form of computer-readable medium, such as a magnetic or optical disk.

The storage device 1506 is capable of providing mass storage for the computing device 1500. In some implementations, the storage device 1506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1502), perform one or more methods, such as those described above. The instructions can also be stored by one or more storage devices such as computer- or machine-readable mediums (for example, the memory 1504, the storage device 1506, or memory on the processor 1502).

The high-speed interface 1508 manages bandwidth-intensive operations for the computing device 1500, while the low-speed interface 1512 manages lower bandwidth-intensive operations. Such allocation of functions is an example only. In some implementations, the high-speed interface 1508 is coupled to the memory 1504, the display 1516 (e.g., through a graphics processor or accelerator), and to the high-speed expansion ports 1510, which may accept various expansion cards (not shown). In the implementation, the low-speed interface 1512 is coupled to the storage device 1506 and the low-speed expansion port 1514. The low-speed expansion port 1514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1520, or multiple times in a group of such servers. In addition, it may be implemented in a personal computer such as a laptop computer 1522. It may also be implemented as part of a rack server system 1524. Alternatively, components from the computing device 1500 may be combined with other components in a mobile device (not shown), such as a mobile computing device 1550. Each of such devices may contain one or more of the computing device 1500 and the mobile computing device 1550, and an entire system may be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 may also be provided with a storage device, such as a micro-drive or other device, to provide additional storage. Each of the processor 1552, the memory 1564, the display 1554, the communication interface 1566, and the transceiver 1568, are interconnected using various buses, and several of the components may be mounted on a common motherboard or in other manners as appropriate.

The processor 1552 can execute instructions within the mobile computing device 1550, including instructions stored in the memory 1564. The processor 1552 may be implemented as a chipset of chips that include separate and multiple analog and digital processors. The processor 1552 may provide, for example, for coordination of the other components of the mobile computing device 1550, such as control of user interfaces, applications run by the mobile computing device 1550, and wireless communication by the mobile computing device 1550.

The processor 1552 may communicate with a user through a control interface 1558 and a display interface 1556 coupled to the display 1554. The display 1554 may be, for example, a TFT (Thin-Film-Transistor Liquid Crystal Display) display or an OLED (Organic Light Emitting Diode) display, or other appropriate display technology. The display interface 1556 may comprise appropriate circuitry for driving the display 1554 to present graphical and other information to a user. The control interface 1558 may receive commands from a user and convert them for submission to the processor 1552. In addition, an external interface 1562 may provide communication with the processor 1552, so as to enable near area communication of the mobile computing device 1550 with other devices. The external interface 1562 may provide, for example, for wired communication in some implementations, or for wireless communication in other implementations, and multiple interfaces may also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 may also be provided and connected to the mobile computing device 1550 through an expansion interface 1572, which may include, for example, a SIMM (Single In Line Memory Module) card interface. The expansion memory 1574 may provide extra storage space for the mobile computing device 1550, or may also store applications or other information for the mobile computing device 1550. Specifically, the expansion memory 1574 may include instructions to carry out or supplement the processes described above, and may include secure information also. Thus, for example, the expansion memory 1574 may be provided as a security module for the mobile computing device 1550, and may be programmed with instructions that permit secure use of the mobile computing device 1550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1552), perform one or more methods, such as those described above. The instructions can also be stored by one or more storage devices, such as one or more computer- or machine-readable mediums (for example, the memory 1564, the expansion memory 1574, or memory on the processor 1552). In some implementations, the instructions can be received in a propagated signal, for example, over the transceiver 1568 or the external interface 1562.

The mobile computing device 1550 may communicate wirelessly through the communication interface 1566, which may include digital signal processing circuitry where necessary. The communication interface 1566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1568 using a radio-frequency. In addition, short-range communication may occur, such as using a Bluetooth®, Wi-Fi™, or other such transceiver (not shown). In addition, a GPS (Global Positioning System) receiver module 1570 may provide additional navigation- and location-related wireless data to the mobile computing device 1550, which may be used as appropriate by applications running on the mobile computing device 1550.

The mobile computing device 1550 may also communicate audibly using an audio codec 1560, which may receive spoken information from a user and convert it to usable digital information. The audio codec 1560 may likewise generate audible sound for a user, such as through a speaker, e.g., in a handset of the mobile computing device 1550. Such sound may include sound from voice telephone calls, may include recorded sound (e.g., voice messages, music files, etc.) and may also include sound generated by applications operating on the mobile computing device 1550.

The mobile computing device 1550 may be implemented in a number of different forms, as shown in the figure. For example, it may be implemented as a cellular telephone 1580. It may also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method comprising:
   receiving, by a processor of a computing device, a 3-D image of a 3-D object representing a bone of interest of a mammal, wherein the 3-D object comprises at least a surface of the bone of interest and at least an internal voxel;
   generating, by the processor, a filled bone mask of the bone of interest, wherein the filled bone mask includes at least the surface of the bone of interest and at least the internal voxel;
   generating, by the processor, a skeleton of the filled bone mask to produce a plurality of branches through the 3-D object; and
   determining, by the processor, a 3-D central axis of the bone of interest, wherein the 3-D central axis corresponds to a medial path through the 3-D object.

2. The method of claim 1, further comprising:
   generating, by the processor, a binary bone mask of the bone of interest; and
   generating, by the processor, the filled bone mask for the bone of interest using the binary bone mask.

3. The method of claim 1, wherein the 3-D image is obtained by a computed tomography scanner.

4. The method of claim 1, wherein the surface of the bone of interest is an exterior surface of cortical tissue of the one or more bones.

5. The method of claim 1, wherein generating the filled bone mask for the bone of interest further comprises
   performing, by the processor, morphological processing of the 3-D object representing the bone of interest, said morphological processing comprising:
      generating, by the processor, a binary bone mask of the bone of interest; and
      performing 3-D binary dilation of the binary bone mask of the bone of interest to form a dilated bone mask; and
      identifying and filling borders, internal voxels, and/or morphological holes of the dilated bone mask, and then processing the result to generate the filled bone mask for the bone of interest.

6. The method of claim 5, wherein the morphological processing further comprises:
   performing 3-D binary dilation of the binary bone mask of the bone of interest to form a dilated bone mask; and
   wherein the identifying and filling borders, internal voxels, and/or morphological holes of the bone mask further comprises
      identifying and filling borders, internal voxels, and/or morphological holes of the dilated bone mask.

7. The method of claim 5, wherein filling borders of the bone of interest further comprises:
   representing image data from the binary bone mask of the bone of interest digitally as one or more data-cubes;
   identifying a vertex of a data-cube, the vertex having all edges connected to the vertex associated with true voxels;
   forming a 2-D image from the three faces connected to the identified vertex of the data-cube;
   filling morphological holes in the thusly formed 2-D image to produce a filled surface; and
   mapping the filled surface back to the three faces connected to the identified vertex of the data-cube.

8. The method of claim 1, wherein generating the skeleton of the bone of interest comprises performing, by the processor, morphological processing of the filled bone mask.

9. The method of claim 1, wherein the determining the 3-D central axis of the bone of interest further comprises:
   generating, by the processor, a thinned skeleton of the bone of interest.

10. The method of claim 9, wherein generating the thinned skeleton further comprises:
    identifying a single-branched centerline tree or a single-cycle main loop of the skeleton as a main path;
    removing minor branches not included in the main path; and
    smoothing the resulting skeleton with the removed minor branches, thereby generating the thinned skeleton.

11. The method of claim 1, further comprising:
    characterizing the bone of interest according to the 3-D central axis corresponding to the bone of interest.

12. The method of claim 1, further comprising:
    rendering an image using at least the 3-D central axis of the bone of interest.

13. The method of claim 1, further comprising:
    performing, by the processor, a stereological measurement of the bone of interest using the determined 3-D central axis of the bone of interest, said performing of the stereological measurement comprising:
    producing a plurality of graphical 2-D cross-sections of the bone of interest in planes perpendicular to the determined 3-D central axis at various locations along a length of the bone of interest;
    for each of the graphical 2-D cross-sections, determining a measurement of the bone as depicted in the graphical 2-D cross section; and
    obtaining the stereological measurement of the bone of interest using the measurements determined from the plurality of graphical 2-D cross-sections.

14. The method of claim 1, further comprising:
    determining, by the processor and using the determined 3-D central axis of the bone of interest, one or more of: (i) a presence of a disease state, (ii) a disease state risk, or (iii) an extent of disease progression.

15. A system comprising:
    a processor; and
    a memory having instructions stored thereon, wherein the instructions, when executed by the processor, cause the processor to:
       receive, by a processor of a computing device, a 3-D image of a 3-D object representing a bone of interest of a mammal, wherein the 3-D object comprises at least a surface of the bone of interest and at least an internal voxel;
       generate, by the processor, a filled bone mask of the bone of interest, wherein the filled bone mask includes at least the surface of the bone of interest and at least the internal voxel;
       generate, by the processor, a skeleton of the filled bone mask; and
       determine, by the processor, the 3-D central axis of the bone of interest, wherein the 3-D central axis corresponds to a medial path through the 3-D object.

16. The system of claim 15,
    generating, by the processor, a binary bone mask of the bone of interest; and
    generating, by the processor, the filled bone mask for the bone of interest using the binary bone mask.

17. The system of claim 15, wherein generating the filled bone mask for the bone of interest further comprises:
  performing, by the processor, morphological processing of the 3-D object representing the bone of interest, said morphological processing comprising:
    generating, by the processor, a binary bone mask of the bone of interest; and
    performing 3-D binary dilation of the binary bone mask of the bone of interest to form a dilated bone mask; and
    identifying and filling borders, internal voxels, and/or morphological holes of the dilated bone mask, and then processing the result to generate the filled bone mask for the bone of interest.

18. The system of claim 17, wherein filling borders of the bone of interest further comprises:
  representing image data from the binary bone mask of the bone of interest digitally as one or more data-cubes;
  identifying a vertex of a data-cube, the vertex having all edges connected to the vertex associated with true voxels;
  forming a 2-D image from the three faces connected to the identified vertex of the data-cube;
  filling morphological holes in the thusly formed 2-D image to produce a filled surface; and
  mapping the filled surface back to the three faces connected to the identified vertex of the data-cube.

19. The system of claim 15, wherein the determining the 3-D central axis of the bone of interest further comprises:
  generating a thinned skeleton of the bone of interest.

20. A non-transitory computer readable storage media comprising computer
  readable instructions that, when executed by a processor, cause a computing device to
    receive a 3-D image of a 3-D object representing a bone of interest of a mammal, wherein the 3-D object comprises at least a surface of the bone of interest and at least an internal voxel;
    generate a filled bone mask of the bone of interest, wherein the filled bone mask includes at least the surface of the bone of interest and at least the internal voxel;
    generate a skeleton of the bone of interest by performing 3D thinning; and
    determine a 3-D central axis of the bone of interest, wherein the 3-D central axis corresponds to a medial path through the 3-D object.

* * * * *